United States Patent
Cerretti et al.

(10) Patent No.: US 6,521,424 B2
(45) Date of Patent: Feb. 18, 2003

(54) RECOMBINANT EXPRESSION OF TEK ANTAGONISTS

(75) Inventors: Douglas P. Cerretti, Seattle, WA (US); William C. Fanslow, III, Normandy Park, WA (US)

(73) Assignee: Immunex Corporation, Seattle, WA (US)

(*) Notice: Subject to any disclaimer, the term of this patent is extended or adjusted under 35 U.S.C. 154(b) by 29 days.

(21) Appl. No.: 09/733,764

(22) Filed: Dec. 7, 2000

(65) Prior Publication Data

US 2002/0039992 A1 Apr. 4, 2002

Related U.S. Application Data

(63) Continuation-in-part of application No. 09/590,656, filed on Jun. 7, 2000, now Pat. No. 6,413,932.
(60) Provisional application No. 60/137,889, filed on Jun. 7, 1999.

(51) Int. Cl.[7] .............................. C12N 15/00
(52) U.S. Cl. ............ 435/69.1; 435/320.1; 435/252.3; 435/325; 435/6; 536/23.5; 530/350
(58) Field of Search ................ 435/69.1, 252.3, 435/320.1, 325, 6; 530/350; 514/2; 536/23.5

(56) References Cited

U.S. PATENT DOCUMENTS

| | | |
|---|---|---|
| 5,447,860 A | 9/1995 | Zeigler |
| 5,681,714 A | 10/1997 | Breitman et al. |
| 5,955,291 A | 9/1999 | Alitalo et al. |
| 5,998,187 A | 12/1999 | Breitman et al. |

FOREIGN PATENT DOCUMENTS

| | | |
|---|---|---|
| EP | 854 185 A2 | 7/1998 |
| JP | 06315382 A | 11/1994 |
| WO | WO 93 14124 | 7/1993 |
| WO | WO 94 00469 | 1/1994 |
| WO | WO 94/10197 | 5/1994 |
| WO | WO 95 13387 | 5/1995 |
| WO | WO 95 21866 | 8/1995 |
| WO | WO 96 11269 | 4/1996 |
| WO | WO 96 31598 | 10/1996 |
| WO | WO 98 18914 | 5/1998 |
| WO | WO 99/43801 | 9/1999 |
| WO | WO 00/18437 | 4/2000 |

OTHER PUBLICATIONS

Denny, T. P. et al., "Cloning and characterization of tek, the gene encoding the major extracellular protein of pseudomonas solanacearum," *Molecular Plant–Microbe Interactions* 9(4):272–281, 1996.

Folkman, J., "Antiangiogenic gene therapy," *Proc. Natl. Acad. Sci.* 95:9064–9066, 1998.

Hanahan, D., "Signaling Vascular Morphogenesis and Maintenance," *Sci.* 277:48, 1997.

Koblizek, T. I. et al., "Tie2 receptor expression and phosphorylation in cultured cells and mouse tissues," *Eur. J. Biochem.* 244:774–779, 1997.

Labrador, J. P. et al., "The N–terminal globular domain of Eph receptors is sufficient for ligand binding and receptor signaling," *The EMBO J.* 16(13):3889–3897, 1997.

Lackmann, M. et al., "Distinct subdomains of the EphA3 receptor mediate ligand binding and receptor dimerization," *J. of Biol. Chem.* 273(32):20228–20237, 1998.

Lin, P. et al., "Inhibition of tumor angiogenesis using a soluble receptor establishes a role for Tie2 in pathologic vascular growth," *J. Clin. Invest.* 100(8):2072–2078, 1997.

Lin, P. et al., "Antiangiogenic gene therapy targeting the endothelium–specific receptor tyrosine kinase Tie2," *Proc. Natl. Acad. Sci.* 95:8829–8834, 1998.

Peters, K. G. et al., "Expression of Tie2/Tek in breast tumour vasculature provides a new marker for evaluation of tumour angiogenesis," *British J. Cancer* 71(1):51–56, 1998.

*Primary Examiner*—Lorraine Spector
*Assistant Examiner*—Dong Jiang
(74) *Attorney, Agent, or Firm*—Julie K. Smith

(57) ABSTRACT

The present invention provides Tek antagonists and methods of inhibiting angiogenesis in a mammal by administering Tek antagonists. The methods are particularly useful in treating diseases or conditions mediated by angiogenesis, such as solid tumors and diseases or conditions characterized by ocular neovascularization. Also provided are materials and methods for recombinant expression of Tek antagonists.

43 Claims, 3 Drawing Sheets

SEQUENCE LISTING

<160> NUMBER OF SEQ ID NOS: 2

<210> SEQ ID NO 1
<211> LENGTH: 977
<212> TYPE: PRT
<213> ORGANISM: Homo sapiens

<400> SEQUENCE: 1

Met Asp Ser Leu Ala Ser Leu Val Leu Cys Gly Val Ser Leu Leu
 1               5                  10                  15

Ser Gly Thr Val Glu Gly Ala Met Asp Leu Ile Leu Ile Asn Ser Leu
            20                  25                  30

-continued

```
Pro Leu Val Ser Asp Ala Glu Thr Ser Leu Thr Cys Ile Ala Ser Gly
         35                  40                  45

Trp Arg Pro His Glu Pro Ile Thr Ile Gly Arg Asp Phe Glu Ala Leu
     50                  55                  60

Met Asn Gln His Gln Asp Pro Leu Glu Val Thr Gln Asp Val Thr Arg
 65                  70                  75                  80

Glu Trp Ala Lys Lys Val Trp Lys Arg Glu Lys Ala Ser Lys Ile
                 85                  90                  95

Asn Gly Ala Tyr Phe Cys Glu Gly Arg Val Arg Gly Glu Ala Ile Arg
             100                 105                 110

Ile Arg Thr Met Lys Met Arg Gln Gln Ala Ser Phe Leu Pro Ala Thr
             115                 120                 125

Leu Thr Met Thr Val Asp Lys Gly Asp Asn Val Asn Ile Ser Phe Lys
 130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                 165                 170                 175

His Leu Pro His Ala Gln Pro Gln Asp Ala Gly Val Tyr Ser Ala Arg
             180                 185                 190

Tyr Ile Gly Gly Asn Leu Phe Thr Ser Ala Phe Thr Arg Leu Ile Val
             195                 200                 205

Arg Arg Cys Glu Ala Gln Lys Trp Gly Pro Glu Cys Asn His Leu Cys
             210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                 245                 250                 255

Leu His Thr Phe Gly Arg Thr Cys Lys Glu Arg Cys Ser Gly Gln Glu
             260                 265                 270

Gly Cys Lys Ser Tyr Val Phe Cys Leu Pro Asp Pro Tyr Gly Cys Ser
             275                 280                 285

Cys Ala Thr Gly Trp Lys Gly Leu Gln Cys Asn Glu Ala Cys His Pro
 290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                 325                 330                 335

Gly Leu Gln Cys Glu Arg Glu Gly Ile Pro Arg Met Thr Pro Lys Ile
             340                 345                 350

Val Asp Leu Pro Asp His Ile Glu Val Asn Ser Gly Lys Phe Asn Pro
             355                 360                 365

Ile Cys Lys Ala Ser Gly Trp Pro Leu Pro Thr Asn Glu Glu Met Thr
 370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                 405                 410                 415

Pro Asp Ser Gly Val Trp Val Cys Ser Val Asn Thr Val Ala Gly Met
             420                 425                 430

Val Glu Lys Pro Phe Asn Ile Ser Val Lys Val Leu Pro Lys Pro Leu
             435                 440                 445
```

-continued

```
Asn Ala Pro Asn Val Ile Asp Thr Gly His Asn Phe Ala Val Ile Asn
450                 455                 460
Ile Ser Ser Glu Pro Tyr Phe Gly Asp Gly Pro Ile Lys Ser Lys Lys
465                 470                 475                 480
Leu Leu Tyr Lys Pro Val Asn His Tyr Glu Ala Trp Gln His Ile Gln
            485                 490                 495
Val Thr Asn Glu Ile Val Thr Leu Asn Tyr Leu Glu Pro Arg Thr Glu
                500                 505                 510
Tyr Glu Leu Cys Val Gln Leu Val Arg Arg Gly Glu Gly Gly Glu Gly
            515                 520                 525
His Pro Gly Pro Val Arg Arg Phe Thr Thr Ala Ser Ile Gly Leu Pro
530                 535                 540
Pro Pro Arg Gly Leu Asn Leu Leu Pro Lys Ser Gln Thr Thr Leu Asn
545                 550                 555                 560
Leu Thr Trp Gln Pro Ile Phe Pro Ser Ser Glu Asp Asp Phe Tyr Val
                565                 570                 575
Glu Val Glu Arg Arg Ser Val Gln Lys Ser Asp Gln Gln Asn Ile Lys
            580                 585                 590
Val Pro Gly Asn Leu Thr Ser Val Leu Leu Asn Asn Leu His Pro Arg
            595                 600                 605
Glu Gln Tyr Val Val Arg Ala Arg Val Asn Thr Lys Ala Gln Gly Glu
610                 615                 620
Trp Ser Glu Asp Leu Thr Ala Trp Thr Leu Ser Asp Ile Leu Pro Pro
625                 630                 635                 640
Gln Pro Glu Asn Ile Lys Ile Ser Asn Ile Thr His Ser Ser Ala Val
                645                 650                 655
Ile Ser Trp Thr Ile Leu Asp Gly Tyr Ser Ile Ser Ser Ile Thr Ile
            660                 665                 670
Arg Tyr Lys Val Gln Gly Lys Asn Glu Asp Gln His Val Asp Val Lys
            675                 680                 685
Ile Lys Asn Ala Thr Ile Ile Gln Tyr Gln Leu Lys Gly Leu Glu Pro
690                 695                 700
Glu Thr Ala Tyr Gln Val Asp Ile Phe Ala Glu Asn Asn Ile Gly Ser
705                 710                 715                 720
Ser Asn Pro Ala Phe Ser His Glu Leu Val Thr Leu Pro Glu Ser Gln
                725                 730                 735
Ala Pro Ala Asp Leu Gly Gly Gly Lys Glu Pro Lys Ser Cys Asp Lys
            740                 745                 750
Thr His Thr Cys Pro Pro Cys Pro Ala Pro Glu Leu Leu Gly Gly Pro
            755                 760                 765
Ser Val Phe Leu Phe Pro Pro Lys Pro Lys Asp Thr Leu Met Ile Ser
770                 775                 780
Arg Thr Pro Glu Val Thr Cys Val Val Val Asp Val Ser His Glu Asp
785                 790                 795                 800
Pro Glu Val Lys Phe Asn Trp Tyr Val Asp Gly Val Glu Val His Asn
                805                 810                 815
Ala Lys Thr Lys Pro Arg Glu Glu Gln Tyr Asn Ser Thr Tyr Arg Val
            820                 825                 830
Val Ser Val Leu Thr Val Leu His Gln Asp Trp Leu Asn Gly Lys Glu
            835                 840                 845
Tyr Lys Cys Lys Val Ser Asn Lys Ala Leu Pro Ala Pro Ile Glu Lys
850                 855                 860
Thr Ile Ser Lys Ala Lys Gly Gln Pro Arg Glu Pro Gln Val Tyr Thr
```

```
                  865                 870                 875                 880

Leu Pro Pro Ser Arg Glu Glu Met Thr Lys Asn Gln Val Ser Leu Thr
                885                 890                 895

Cys Leu Val Lys Gly Phe Tyr Pro Ser Asp Ile Ala Val Glu Trp Glu
            900                 905                 910

Ser Asn Gly Gln Pro Glu Asn Asn Tyr Lys Thr Thr Pro Pro Val Leu
        915                 920                 925

Asp Ser Asp Gly Ser Phe Phe Leu Tyr Ser Lys Leu Thr Val Asp Lys
    930                 935                 940

Ser Arg Trp Gln Gln Gly Asn Val Phe Ser Cys Ser Val Met His Glu
945                 950                 955                 960

Ala Leu His Asn His Tyr Thr Gln Lys Ser Leu Ser Leu Ser Pro Gly
                965                 970                 975

Lys

<210> SEQ ID NO 2
<211> LENGTH: 704
<212> TYPE: PRT
<213> ORGANISM: Homo sapiens

<400> SEQUENCE: 2

Met Asp Ser Leu Ala Ser Leu Val Leu Cys Gly Val Ser Leu Leu Leu
  1               5                  10                  15

Ser Gly Thr Val Glu Gly Ala Met Asp Leu Ile Leu Ile Asn Ser Leu
                 20                  25                  30

Pro Leu Val Ser Asp Ala Glu Thr Ser Leu Thr Cys Ile Ala Ser Gly
             35                  40                  45

Trp Arg Pro His Glu Pro Ile Thr Ile Gly Arg Asp Phe Glu Ala Leu
     50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
```

-continued

```
                260                 265                 270
Gly Cys Lys Ser Tyr Val Phe Cys Leu Pro Asp Pro Tyr Gly Cys Ser
                275                 280                 285
Cys Ala Thr Gly Trp Lys Gly Leu Gln Cys Asn Glu Ala Cys His Pro
            290                 295                 300
Gly Phe Tyr Gly Pro Asp Cys Lys Leu Arg Cys Ser Cys Asn Asn Gly
305                 310                 315                 320
Glu Met Cys Asp Arg Phe Gln Gly Cys Leu Cys Ser Pro Gly Trp Gln
                325                 330                 335
Gly Leu Gln Cys Glu Arg Glu Gly Ile Pro Arg Met Thr Pro Lys Ile
            340                 345                 350
Val Asp Leu Pro Asp His Ile Glu Val Asn Ser Gly Lys Phe Asn Pro
            355                 360                 365
Ile Cys Lys Ala Ser Gly Trp Pro Leu Pro Thr Asn Glu Glu Met Thr
370                 375                 380
Leu Val Lys Pro Asp Gly Thr Val Leu His Pro Lys Asp Phe Asn His
385                 390                 395                 400
Thr Asp His Phe Ser Val Ala Ile Phe Thr Ile His Arg Ile Leu Pro
                405                 410                 415
Pro Asp Ser Gly Val Trp Val Cys Ser Val Asn Thr Val Ala Gly Met
            420                 425                 430
Val Glu Lys Pro Phe Asn Ile Ser Val Lys Val Leu Pro Lys Pro Leu
            435                 440                 445
Asn Ala Pro Asn Val Ile Asp Thr Gly His Asn Phe Ala Val Ile Asn
        450                 455                 460
Ile Ser Ser Glu Pro Tyr Phe Gly Glu Pro Lys Ser Cys Asp Lys Thr
465                 470                 475                 480
His Thr Cys Pro Pro Cys Pro Ala Pro Glu Leu Leu Gly Gly Pro Ser
                485                 490                 495
Val Phe Leu Phe Pro Pro Lys Pro Lys Asp Thr Leu Met Ile Ser Arg
            500                 505                 510
Thr Pro Glu Val Thr Cys Val Val Val Asp Val Ser His Glu Asp Pro
            515                 520                 525
Glu Val Lys Phe Asn Trp Tyr Val Asp Gly Val Glu Val His Asn Ala
        530                 535                 540
Lys Thr Lys Pro Arg Glu Glu Gln Tyr Asn Ser Thr Tyr Arg Val Val
545                 550                 555                 560
Ser Val Leu Thr Val Leu His Gln Asp Trp Leu Asn Gly Lys Glu Tyr
                565                 570                 575
Lys Cys Lys Val Ser Asn Lys Ala Leu Pro Ala Pro Ile Glu Lys Thr
            580                 585                 590
Ile Ser Lys Ala Lys Gly Gln Pro Arg Glu Pro Gln Val Tyr Thr Leu
        595                 600                 605
Pro Pro Ser Arg Glu Glu Met Thr Lys Asn Gln Val Ser Leu Thr Cys
    610                 615                 620
Leu Val Lys Gly Phe Tyr Pro Ser Asp Ile Ala Val Glu Trp Glu Ser
625                 630                 635                 640
Asn Gly Gln Pro Glu Asn Asn Tyr Lys Thr Thr Pro Pro Val Leu Asp
                645                 650                 655
Ser Asp Gly Ser Phe Phe Leu Tyr Ser Lys Leu Thr Val Asp Lys Ser
            660                 665                 670
Arg Trp Gln Gln Gly Asn Val Phe Ser Cys Ser Val Met His Glu Ala
        675                 680                 685
```

```
Leu His Asn His Tyr Thr Gln Lys Ser Leu Ser Leu Ser Pro Gly Lys
    690                 695                 700
```

RECOMBINANT EXPRESSION OF TEK ANTAGONISTS

REFERENCE TO RELATED APPLICATIONS

This application is a continuation-in-part of pending U.S. application Ser. No. 09/590,656, filed Jun. 7, 2000, now U.S. Pat. No. 6,413,932, and incorporated herein by reference, which claims the benefit of U.S. Provisional Application Serial No. 60/137,889, filed Jun. 7, 1999 and incorporated herein by reference.

FIELD OF THE INVENTION

The present invention relates to Tek antagonists and to the use of Tek antagonists to inhibit angiogenesis or other Tek-mediated responses in a mammal.

BACKGROUND OF THE INVENTION

A. Angiogenesis

Angiogenesis, the generation of new blood vessels, is a spatially and temporally regulated process in which endothelial cells proliferate, migrate, and assemble into tubes, in response to endogenous positive and negative regulatory molecules. Angiogenesis plays important roles in both normal and pathological physiology.

Under normal physiological conditions, angiogenesis is involved in fetal and embryonic development, wound healing, organ regeneration, and female reproductive remodeling processes including formation of the endometrium, corpus luteum, and placenta. Angiogenesis is stringently regulated under normal conditions, especially in adult animals, and perturbation of the regulatory controls can lead to pathological angiogenesis.

Pathological angiogenesis has been implicated in the manifestation and/or progression of inflammatory diseases, certain eye disorders, and cancer. In particular, several lines of evidence support the concept that angiogenesis is essential for the growth and persistence of solid tumors and their metastases (see, e.g., Folkman, N. Engl. J. Med. 285:1182, 1971; Folkman et al., Nature 339:58, 1989; Kim et al., Nature 362:841, 1993; Hori et al., Cancer Res., 51:6180, 1991). Angiogenesis inhibitors are therefore being tested for the prevention (e.g., treatment of premalignant conditions), intervention (e.g., treatment of small tumors), and regression (e.g., treatment of large tumors) of cancers (see, e.g., Bergers et al., Science 284:808, 1999).

Although several anti-angiogenic agents are presently under development and testing as therapeutics, there is a need for additional methods of inhibiting angiogenesis for the prevention, abrogation, and mitigation of disease processes that are dependent on pathological angiogenesis.

B. Tek Polypeptides

The receptor tyrosine kinases (RTKs) are a large and evolutionarily conserved family of proteins involved in the transduction of extracellular signals to the cytoplasm. Among the RTKs believed to be involved in vascular morphogenesis and maintenance are the vascular endothelial growth factor (VEGF) receptors and Tek (see Hanahan, Science 277:48, 1997).

Tek, which has also been called Tie2 and ork, is an RTK that is predominantly expressed in vascular endothelium. The molecular cloning of human Tek (ork) has been described by Ziegler, U.S. Pat. No. 5,447,860. Four Tek ligands, angiopoietin-1, angiopoietin-2, angiopoietin-3, and angiopoietin-4 (Ang1, Ang2, Ang3, and Ang4), have been described (Davis et al., Cell 87:1161, 1996; Maisonpierre et al., Science 277:55, 1997; Valenzuela et al., Proc. Natl. Acad. Sci. USA 96:1904, 1999). These ligands have distinct expression patterns and activities with respect to Tek. "Tie ligand homologues" designated NL1, NL5, NL8, and NL4 are described in U.S. Pat. No. 6,057,435.

Tek knockout mice have defects in vascular development, and die during embryogenesis (see Dumont, Genes Dev. 8:1897, 1994; Sato, Nature 376:70, 1995), suggesting that Tek plays a role in the development of embryonic vasculature.

Lin et al. have described a soluble Tek (Tie2) inhibitor designated ExTek.6His, consisting of the entire extracellular portion of murine Tek fused to a six-histidine tag (J. Clin. Invest. 100(8):2072, 1997; WO 98/18914). ExTek.6His inhibited growth and tumor vascularization in a rat cutaneous window chamber model, and blocked angiogenesis stimulated by tumor cell conditioned media in a rat corneal micropocket assay. Peters et al. have also described a replication-defective adenoviral vector designated AdExTek, which expresses the murine Tek extracellular domain (Proc. Natl. Acad. Sci. USA 95:8829, 1998; WO 98/18914). AdExTek inhibited the growth and metastasis of a murine mammary carcinoma and a murine melanoma.

While ExTek.6His and AdExTek may prove useful as anti-angiogenic agents, there is a need for additional and improved Tek antagonists and additional and improved methods of inhibiting angiogenesis or other Tek-mediated responses using Tek antagonists.

SUMMARY OF THE INVENTION

The present invention provides Tek antagonists and methods of using Tek antagonists to inhibit angiogenesis or other Tek-mediated responses in a mammal in need of such treatment. The invention is based in part on the unexpected discovery that fragments of the Tek extracellular domain, lacking all or part of the region containing fibronectin type III (FNIII) motifs, can have a higher binding affinity for Tek ligands than polypeptides comprising full length Tek extracellular domain.

In some preferred embodiments the Tek antagonist is a polypeptide comprising a fragment of Tek extracellular domain, wherein the fragment lacks all or part of the region containing fibronectin type III (FNIII) motifs and wherein the polypeptide retains the ability to bind at least one Tek ligand. In preferred embodiments the fragment lacks at least residues 473–745 of the Tek extracellular domain; in more preferred embodiments the Tek ligand is angiopoietin-1, angiopoietin-2, or angiopoietin-4. In most preferred embodiments, the Tek antagonist is a polypeptide that has a higher binding affinity for a Tek ligand than does a polypeptide comprising full length Tek extracellular domain.

The invention also encompasses nucleic acids encoding polypeptides according to the invention, and polypeptides produced by expressing such a nucleic acid in a recombinant host cell under conditions that permit expression of the polypeptide.

In some preferred embodiments, the Tek antagonist is a soluble Tek multimer, preferably a dimer or trimer, and most preferably comprising an Fc polypeptide or a leucine zipper. The Tek is preferably human Tek. In some preferred embodiments the soluble Tek multimer comprises a fragment of Tek extracellular domain, wherein the fragment lacks all or part of the region containing fibronectin type III (FNIII) motifs and wherein the polypeptide retains the ability to bind at least one Tek ligand. In some preferred embodiments the soluble Tek multimer comprises residues 23–472 or 23–704 of SEQ ID NO:2.

The invention also encompasses antibodies or antibody fragments that bind specifically to a polypeptide according to the invention, and antibodies or antibody fragments that are capable of competitively inhibiting the binding of a Tek ligand to a polypeptide according to the invention. The antibodies are preferably selected from the group consisting of monoclonal antibodies, humanized antibodies, transgenic antibodies, and human antibodies.

The invention also provides methods of inhibiting angiogenesis or other Tek-mediated responses in a mammal in need of such treatment, comprising administering to the mammal an inhibition-effective amount of a Tek antagonist. The Tek antagonist is preferably a fragment of Tek extracellular domain, a soluble Tek multimer, or an antibody or antibody fragment. In some preferred embodiments the Tek antagonist is administered in a composition comprising a pharmaceutically acceptable carrier.

The soluble Tek multimer is preferably administered to a mammal that has a disease or condition mediated by angiogenesis, more preferably a solid tumor or a disease or condition characterized by ocular neovascularization.

In some embodiments the method further comprises treating the mammal with a second chemotherapeutic agent and or with radiation. The second chemotherapeutic agent may be selected from the group consisting of alkylating agents, antimetabolites, vinca alkaloids and other plant-derived chemotherapeutics, nitrosoureas, antitumor antibiotics, antitumor enzymes, topoisomerase inhibitors, platinum analogs, adrenocortical suppressants, hormones, hormone agonists, hormone antagonists, antibodies, immunotherapeutics, blood cell factors, radiotherapeutics, and biological response modifiers, and more preferably selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, and vinblastine, lymphokines and cytokines such as interleukins, interferons (including alpha, beta, or delta), and TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, and fluoxymesterone, Flt3 ligand, CD40 ligand, interleukin-2, interleukin-12, 4-1BB ligand, anti-4-1BB antibodies, TNF antagonists and TNF receptor antagonists including TNFR/Fc, TWEAK antagonists and TWEAK-R antagonists including TWEAK-R/Fc, TRAIL, CD148 agonists, VEGF antagonists including anti-VEGF antibodies, and VEGF receptor antagonists.

The invention is further directed to a method of inhibiting the binding of a Tek ligand to Tek in a mammal in need of such treatment, comprising administering to the mammal an inhibition-effective amount of a Tek antagonist. The Tek antagonist is preferably a fragment of Tek extracellular domain, a soluble Tek multimer, or an antibody or antibody fragment.

The invention is also directed to the use of a Tek antagonist for the preparation of a medicament for inhibiting angiogenesis in a mammal in need of such treatment, or for inhibiting the binding of a Tek ligand to Tek in a mammal in need of such treatment. The Tek antagonist is preferably a fragment of Tek extracellular domain, a soluble Tek multimer, or an antibody or antibody fragment.

These and other aspects of the present invention will become evident upon reference to the following drawings and detailed description.

DETAILED DESCRIPTION OF THE INVENTION

Figure 1:
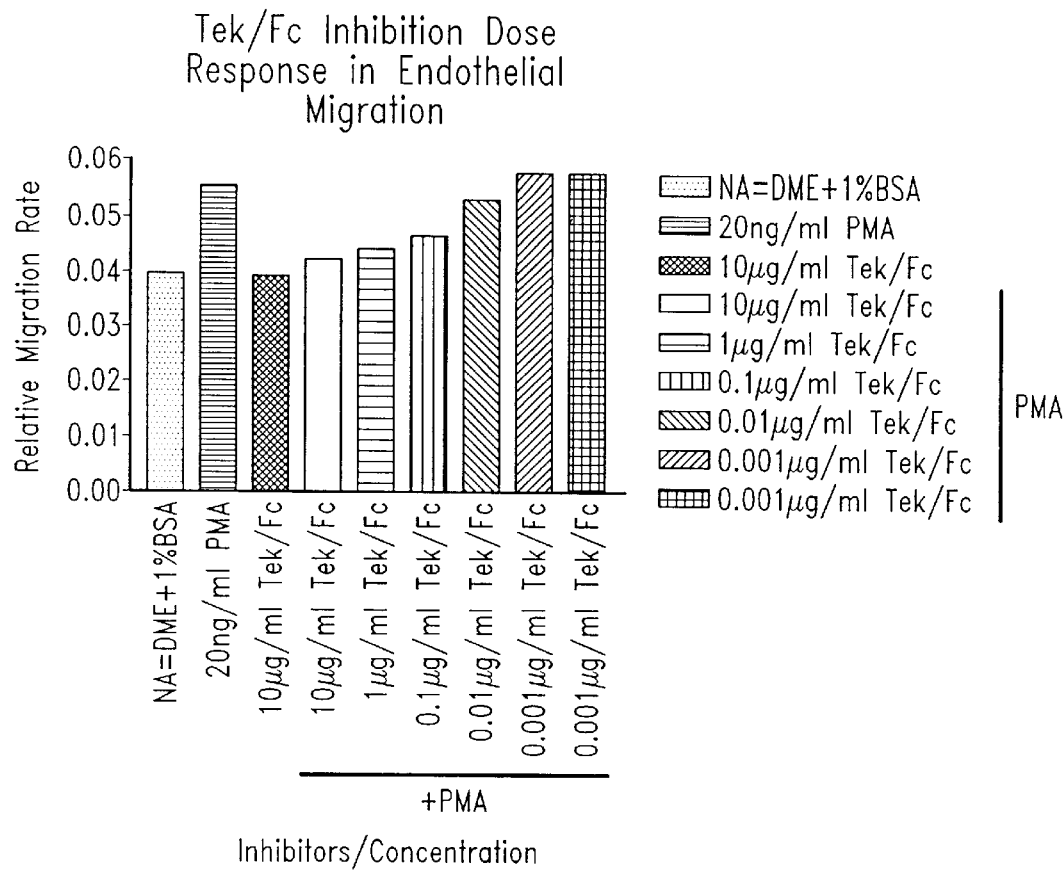
FIG. 1 shows inhibition by Tek472/Fc of endothelial cell migration in a wound closure assay.

The present invention is directed to Tek antagonists and methods of using Tek antagonists to inhibit angiogenesis or other Tek-mediated responses in a mammal. Tek antagonists are compounds or compositions that interfere with one or more biological activities of Tek, including ligand binding and signal transduction, and may be characterized using methods such as those exemplified below. Tek antagonists include fragments of the Tek extracellular domain, soluble Tek multimers, and Tek antibodies and antibody fragments. The molecular cloning of a cDNA encoding human Tek (ork, Tie2) is described in U.S. Pat. No. 5,447,860.

A. Abbreviations and Terminology Used in the Specification

"4-1BB" and "4-1BB ligand" (4-1BB-L) are polypeptides described, inter alia, in U.S. Pat. No. 5,674,704, including soluble forms thereof.

"bFGF" is basic fibroblast growth factor.

"BSA" is bovine serum albumin.

"CD40 ligand" (CD40L) is a polypeptide described, inter alia, in U.S. Pat. No. 5,716,805, including soluble forms thereof.

"CHO" is a Chinese hamster ovary cell line.

"DMEM" is Dulbecco's Modified eagle Medium, a commercially available cell culture medium.

"ELISA" is Enzyme-Linked Immunosorbent Assay.

"Flt3L" is Flt3 ligand, a polypeptide described, inter alia, in U.S. Pat. No. 5,554,512, including soluble forms thereof.

"HMVEC-d" are primary dermal human microvascular endothelial cells.

"HRMEC" are primary human renal microvascular endothelial cells.

"HUVEC" is a line of human umbilical vein endothelial cells.

"mAb" is a monoclonal antibody.

"MSA" is mouse serum albumin.

"PBS" is phosphate buffered saline.

"PE" is phycoerythrin.

"PMA" is phorbol 12-myristate-13-acetate.

"RTKs" are receptor tyrosine kinases.

"TNFR" is a tumor necrosis factor receptor, including soluble forms thereof. "TNFR/Fc" is a tumor necrosis factor receptor-Fc fusion polypeptide.

"TRAIL" is TNF-related apoptosis-inducing ligand, a type II transmembrane polypeptide in the TNF family described, inter alia, in U.S. Pat. No. 5,763,223, including soluble forms thereof.

"TWEAK" is TNF-weak effector of apoptosis, a type II transmembrane polypeptide in the TNF family described, inter alia, in Chicheportiche et al., J. Biol. Chem., 272(51): 32401, 1997, including soluble forms thereof. "TWEAK-R" is the "TWEAK receptor," which is described, inter alia, in U.S. Ser. Nos. 60/172,878 and 60/203,347 and Feng et al., Am. J. Pathol. 156(4):1253, 2000, including soluble forms thereof.

"VEGF" is vascular endothelial growth factor, also known as VPF or vascular permeability factor.

B. Soluble Tek Polypeptides

In one aspect of the present invention, a soluble Tek polypeptide is used as a Tek antagonist to inhibit angiogenesis or to inhibit the binding of a Tek ligand to Tek.

Soluble polypeptides are capable of being secreted from the cells in which they are expressed. The use of soluble forms of polypeptides is advantageous for certain applications. Purification of the polypeptides from recombinant host cells is facilitated since the polypeptides are secreted, and soluble proteins are generally suited for parenteral administration. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. Soluble polypeptides may be prepared by any of a number of conventional techniques. A DNA sequence encoding a desired soluble polypeptide may be subcloned into an expression vector for production of the polypeptide, or the desired encoding DNA fragment may be chemically synthesized.

Soluble Tek polypeptides comprise all or part of the Tek extracellular domain, but generally lack the transmembrane domain that would cause retention of the polypeptide at the cell surface. Soluble polypeptides may include part of the transmembrane domain or all or part of the cytoplasmic domain as long as the polypeptide is secreted from the cell in which it is produced. Soluble Tek polypeptides advantageously comprise a native or heterologous signal peptide when initially synthesized, to promote secretion from the cell, but the signal sequence is cleaved upon secretion. The term "Tek extracellular domain" is intended to encompass all or part of the native Tek extracellular domain, as well as related forms including but not limited to: (a) fragments, (b) variants, (c) derivatives, and (d) fusion polypeptides. The ability of these related forms to inhibit angiogenesis or other Tek-mediated responses may be determined in vitro or in vivo, using methods such as those exemplified below or using other assays known in the art.

Examples of soluble Tek polypeptides are provided the examples below. As described in the examples, the Inventors unexpectedly discovered that certain fragments of the Tek extracellular domain bind Tek ligands better than the full length Tek extracellular domain, that these fragments can therefore be used as antagonists to block the binding of Tek ligands to Tek (for example, the Tek found on a cell surface), and that antibodies to these fragments can also be used as antagonists to block the binding of Tek ligands to Tek. In some embodiments of the present invention a multimeric form of a soluble Tek polypeptide ("soluble Tek multimer") is used as an antagonist to block the binding of Tek ligands to Tek, to inhibit angiogenesis or other Tek-mediated responses.

C. Soluble Tek Multimers

Soluble Tek multimers are covalently-linked or non-covalently-linked multimers, including dimers, trimers, or higher multimers. Multimers may be linked by disulfide bonds formed between cysteine residues on different soluble Tek polypeptides. One embodiment of the invention is directed to multimers comprising multiple soluble Tek polypeptides joined via covalent or non-covalent interactions between peptide moieties fused to the soluble Tek polypeptides. Such peptides may be peptide linkers (spacers), or peptides that have the property of promoting multimerization. Leucine zippers and certain polypeptides derived from antibodies are among the peptides that can promote multimerization of soluble Tek polypeptides attached thereto, as described in more detail below. In particular embodiments, the multimers comprise from two to four soluble Tek polypeptides.

In some embodiments, a soluble Tek multimer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (Proc. Natl. Acad. Sci. USA 88:10535, 1991); Byrn et al. (Nature 344:677, 1990); and Hollenbaugh and Aruffo ("Construction of Immunoglobulin Fusion Proteins", in Current Protocols in Immunology, Suppl. 4, pages 10.19.1–10.19.11, 1992).

One preferred embodiment of the present invention is directed to a Tek/Fc dimer comprising two fusion proteins created by fusing soluble Tek to an Fc polypeptide. A gene fusion encoding the Tek/Fc fusion protein is inserted into an appropriate expression vector. Tek/Fc fusion proteins are expressed in host cells transformed with the recombinant expression vector, and allowed to assemble much like antibody molecules, whereupon interchain disulfide bonds form between the Fc moieties to yield divalent soluble Tek. The term "Fc polypeptide" as used herein includes native and mutein forms of polypeptides derived from the Fc region of an antibody. Truncated forms of such polypeptides containing the hinge region that promotes dimerization are also included.

One suitable Fc polypeptide, described in PCT application WO 93/10151, is a single chain polypeptide extending from the N-terminal hinge region to the native C-terminus of the Fc region of a human IgG1 antibody. Another useful Fc polypeptide is the Fc mutein described in U.S. Pat. No. 5,457,035 and by Baum et al., EMBO J. 13:3992, 1994. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. Fusion polypeptides comprising Fc moieties, and multimers formed therefrom, offer an advantage of facile purification by affinity chromatography over Protein A or Protein G columns, and Fc fusion polypeptides may provide a longer in vivo half life, which is useful in therapeutic applications, than unmodified polypeptides.

In other embodiments, a soluble Tek polypeptide may be substituted for the variable portion of an antibody heavy or light chain. If fusion proteins are made with both heavy and light chains of an antibody, it is possible to form a soluble Tek multimer with as many as four soluble Tek polypeptides.

Alternatively, the soluble Tek multimer is a fusion protein comprising multiple soluble Tek polypeptides, with or without peptide linkers (spacers), or peptides that have the property of promoting multimerization. Among the suitable peptide linkers are those described in U.S. Pat. Nos. 4,751,180, 4,935,233, and 5,073,627. A DNA sequence encoding a desired peptide linker may be inserted between, and in the same reading frame as, the DNA sequences encoding Tek, using conventional techniques known in the art. For example, a chemically synthesized oligonucleotide encoding the linker may be ligated between sequences encoding soluble Tek. In particular embodiments, a fusion protein comprises from two to four soluble Tek polypeptides, separated by peptide linkers.

Another method for preparing soluble Tek multimers involves use of a leucine zipper domain. Leucine zipper domains are peptides that promote multimerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize. Examples of leucine zipper domains suitable for producing soluble multimeric proteins are described in PCT application WO 94/10308, and the leucine zipper derived from lung surfactant protein D (SPD) described in Hoppe et al. FEBS Lett. 344:191, 1994. The use of a modified leucine zipper that allows for stable trimerization of a heterologous protein fused thereto is described in Fanslow et al., Semin. Immunol. 6:267, 1994. Recombinant fusion proteins comprising a soluble Tek polypeptide fused to a leucine zipper peptide are expressed in suitable host cells, and the soluble Tek multimer that forms is recovered from the culture supernatant.

For some applications, the soluble Tek multimers of the present invention are believed to provide certain advantages over the use of monomeric forms, including the advantage of mimicking the natural interaction between a ligand and a receptor tyrosine kinase (RTK). In general, a dimer ligand will bind and cause dimerization of the RTK (van der Geer et al., Ann. Rev. Cell Biol. 10:251, 1994). This high affinity binding causes transphosphorylation of the RTK and the beginning of the signal transduction process. The binding of a soluble Tek multimer may occur at higher affinity than will a soluble Tek monomer. Fc fusion polypeptides offer an additional advantage in that this form typically exhibits an increased in vivo half life as compared to an unmodified polypeptide.

The present invention encompasses the use of various forms of soluble Tek multimers that retain the ability to inhibit angiogenesis or other Tek-mediated responses. The term "soluble Tek multimer" is intended to encompass multimers containing all or part of the native Tek extracellular domain, as well as related forms including, but not limited to, multimers of: (a) fragments, (b) variants, (c) derivatives, and (d) fusion polypeptides of soluble Tek. The ability of these related forms to inhibit angiogenesis or other Tek-mediated responses may be determined in vitro or in vivo, using methods such as those exemplified in the examples or using other assays known in the art.

Among the soluble Tek polypeptides and soluble Tek multimers useful in practicing the present invention are Tek variants that retain the ability to bind ligand and/or inhibit angiogenesis or other Tek-mediated responses. Such Tek variants include polypeptides that are substantially homologous to native Tek, but which have an amino acid sequence different from that of a native Tek because of one or more deletions, insertions or substitutions. Particular embodiments include, but are not limited to, Tek polypeptides that comprise from one to ten deletions, insertions or substitutions of amino acid residues, when compared to a native Tek sequence. Included as variants of Tek polypeptides are those variants that are naturally occurring, such as allelic forms and alternatively spliced forms, as well as variants that have been constructed by modifying the amino acid sequence of a Tek polypeptide or the nucleotide sequence of a nucleic acid encoding a Tek polypeptide.

Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of Tek. Additional examples include substituting one aliphatic residue for another, such as Ile, Val, Leu, or Ala for one another, or substitutions of one polar residue for another, such as between Lys and Arg; Glu and Asp; or Gln and Asn, or substitutions of one aromatic residue for another, such as Phe, Trp, or Tyr for one another. Other such conservative substitutions, for example, substitutions of entire regions having similar hydrophobicity characteristics, are known in the art.

The native sequence of the full length Tek extracellular domain is set forth as residues 23–745 of SEQ ID NO:1. In some preferred embodiments the Tek variant is at least about 70% identical in amino acid sequence to the amino acid sequence of native Tek; in some preferred embodiments the Tek variant is at least about 80% identical in amino acid sequence to the amino acid sequence of native Tek. In some more preferred embodiments the Tek variant is at least about 90% identical in amino acid sequence to the amino acid sequence of native Tek; in some more preferred embodiments the Tek variant is at least about 95% identical in amino acid sequence to the amino acid sequence of native Tek. In some most preferred embodiments the Tek variant is at least about 98% identical in amino acid sequence to the amino acid sequence of native Tek; in some most preferred embodiments the Tek variant is at least about 99% identical in amino acid sequence to the amino acid sequence of native Tek. Percent identity, in the case of both polypeptides and nucleic acids, may be determined by visual inspection. Percent identity may also be determined using the alignment method of Needleman and Wunsch (J. Mol. Biol. 48:443, 1970) as revised by Smith and Waterman (Adv. Appl. Math 2:482, 1981. Preferably, percent identity is determined by using a computer program, for example, the GAP computer program version 10.x available from the Genetics Computer Group (GCG; Madison, Wis., see also Devereux et al., *Nucl. Acids Res.* 12:387, 1984). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979 for amino acids; (2) a penalty of 30 (amino acids) or 50 (nucleotides) for each gap and an additional 1 (amino acids) or 3 (nucleotides) penalty for each symbol in each gap; (3) no penalty for end gaps; and (4) no maximum penalty for long gaps. Other programs used by one skilled in the art of sequence comparison may also be used. For fragments of Tek, the percent identity is calculated based on that portion of Tek that is present in the fragment.

The present invention further encompasses the use of soluble Tek polypeptides with or without associated native-pattern glycosylation. Tek expressed in yeast or mammalian expression systems (e.g., COS-1 or COS-7 cells) may be similar to or significantly different from a native Tek polypeptide in molecular weight and glycosylation pattern, depending upon the choice of expression system. Expression of Tek polypeptides in bacterial expression systems, such as *E. coli,* provides non-glycosylated molecules. Different host cells may also process polypeptides differentially, resulting in heterogeneous mixtures of polypeptides with variable N- or C-termini.

The primary amino acid structure of soluble Tek polypeptides may be modified to create derivatives by forming covalent or aggregative conjugates with other chemical moieties, such as glycosyl groups, lipids, phosphate, acetyl groups and the like. Covalent derivatives of Tek may be prepared by linking particular functional groups to Tek amino acid side chains or at the N-terminus or C-terminus of a Tek polypeptide.

Fusion polypeptides of soluble Tek that are useful in practicing the invention also include covalent or aggregative conjugates of a Tek polypeptide with other polypeptides added to provide novel polyfunctional entities.

D. Recombinant Production of Tek Polypeptides

Tek polypeptides, including soluble Tek polypeptides, fragments, and fusion polypeptides, used in the present invention may be prepared using a recombinant expression system. Host cells transformed with a recombinant expression vector ("recombinant host cells") encoding the Tek polypeptide are cultured under conditions that promote expression of Tek and the Tek is recovered. Tek polypeptides can also be produced in transgenic plants or animals, or by chemical synthesis.

The invention encompasses nucleic acid molecules encoding the Tek polypeptides used in the invention, including: (a) nucleic acids that encode residues 23–472 of SEQ ID NO:2 and fragments thereof that bind a Tek ligand; (b) nucleic acids that are at least 70%, 80%, 90%, 95%, 98%, or 99% identical to a nucleic acid of (a), and which encode a polypeptide capable of binding at least one Tek ligand; and (c) nucleic acids that hybridize at moderate stringency to a nucleic acid of (a), and which encode a polypeptide capable of binding at least one Tek ligand.

Due to degeneracy of the genetic code, there can be considerable variation in nucleotide sequences encoding the same amino acid sequence. Included as embodiments of the invention are nucleic acid sequences capable of hybridizing under moderately stringent conditions (e.g., prewashing solution of 5×SSC, 0.5% SDS, 1.0 mM EDTA (pH 8.0) and hybridization conditions of 50° C., 5×SSC, overnight) to the DNA sequences encoding Tek. The skilled artisan can determine additional combinations of salt and temperature that constitute moderate hybridization stringency (see also, Sambrook, *Molecular Cloning: A Laboratory Manual,* Cold Spring Harbor Laboratory Press, 1989; Maniatis, *Molecular Cloning: A Laboratory Manual,* Cold Spring Harbor Laboratory Press, 1982; and Ausubel, *Current Protocols in Molecular Biology,* Wiley and Sons, 1989 and later versions, which are incorporated herein by reference). Conditions of higher stringency include higher temperatures for hybridization and post-hybridization washes, and/or lower salt concentration. Percent identity of nucleic acids may be determined using the methods described above for polypeptides, i.e., by methods including visual inspection and the use of computer programs such as GAP.

Any suitable expression system may be employed for the production of recombinant Tek. Recombinant expression vectors include DNA encoding a Tek polypeptide operably linked to suitable transcriptional and translational regulatory nucleotide sequences, such as those derived from a mammalian, microbial, viral, or insect gene. Nucleotide sequences are operably linked when the regulatory sequence functionally relates to the Tek DNA sequence. Thus, a promoter nucleotide sequence is operably linked to a Tek DNA sequence if the promoter nucleotide sequence controls the transcription of the Tek DNA sequence. Examples of regulatory sequences include transcriptional promoters, operators, or enhancers, an mRNA ribosomal binding site, and appropriate sequences which control transcription and translation initiation and termination. A sequence encoding an appropriate signal peptide (native or heterologous) can be incorporated into expression vectors. A DNA sequence for a signal peptide (referred to by a variety of names including secretory leader, leader peptide, or leader) may be fused in frame to the Tek sequence so that the Tek polypeptide is initially translated as a fusion protein comprising the signal peptide. A signal peptide that is functional in the intended host cells promotes extracellular secretion of the Tek polypeptide. The signal peptide is cleaved from the Tek polypeptide upon secretion of Tek from the cell.

Suitable host cells for expression of Tek polypeptides include prokaryotes, yeast and higher eukaryotic cells, including insect and mammalian cells. Appropriate cloning and expression vectors for use with bacterial, fungal, yeast, insect, and mammalian cellular hosts are described, for example, in Pouwels et al. *Cloning Vectors: A Laboratory Manual,* Elsevier, New York, 1985.

Prokaryotes include gram negative or gram positive organisms, for example, *E. coli* or Bacilli. Suitable prokaryotic host cells for transformation include, for example, *E. coli, Bacillus subtilis, Salmonella typhimurium,* and various other species within the genera Pseudomonas, Streptomyces, and Staphylococcus. In a prokaryotic host cell, such as *E. coli,* Tek polypeptides may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker gene(s). A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicilline and tetracycline resistance and thus provides simple means for identifying transformed cells. An appropriate promoter and a Tek DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., Nature 275:615, 1978; Goeddel et al., Nature 281:544, 1979), tryptophan (trp) promoter system (Goeddel et al., Nucl. Acids Res. 8:4057, 1980; EP-A-36776) and tac promoter (Maniatis, *Molecular Cloning: A Laboratory Manual,* Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9, ATCC 37092) and pPLc28 (resident in *E. coli* RR1, ATCC 53082).

Tek polypeptides may also be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (J. Biol. Chem. 258:2674, 1982) and Beier et al. (Nature 300:724, 1982). Shuttle vectors replicable in both yeast and E. coli may be constructed by inserting DNA sequences from pBR322 for selection and replication in E. coli (Amp$^r$ gene and origin of replication) into the above-described yeast vectors.

The yeast α-factor leader sequence may be employed to direct secretion of recombinant polypeptides. The α-factor leader sequence is often inserted between the promoter sequence and the structural gene sequence. See, e.g., Kurjan et al., Cell 30:933, 1982; Bitter et al., Proc. Natl. Acad. Sci. USA 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 µg/ml adenine and 20 µg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Insect host cell culture systems also may be employed to express recombinant Tek polypeptides, including soluble Tek polypeptides. Bacculovirus systems for production of heterologous polypeptides in insect cells are reviewed by Luckow and Summers, Bio/Technology 6:47, 1988.

Mammalian cells are particularly preferred for use as host cells. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (EMBO J. 10: 2821, 1991). For the production of therapeutic polypeptides it is particularly advantageous to use a mammalian host cell line which has been adapted to grow in media that does not contain animal proteins.

Established methods for introducing DNA into mammalian cells have been described (Kaufman, R. J., Large Scale Mammalian Cell Culture, 1990, pp.15–69). Additional protocols using commercially available reagents, such as Lipofectamine (Gibco/BRL) or Lipofectamine-Plus, can be used to transfect cells (Felgner et al., Proc. Natl. Acad. Sci. USA 84:7413, 1987). In addition, electroporation can be used to transfect mammalian cells using conventional procedures, such as those in Sambrook et al. Molecular Cloning: A Laboratory Manual, 2 ed. Vol. 1–3, Cold Spring Harbor Laboratory Press, 1989). Selection of stable transformants can be performed using methods known in the art, such as, for example, resistance to cytotoxic drugs. Kaufman et al., Meth. in Enzymology 185:487, 1990, describes several selection schemes, such as dihydrofolate reductase (DHFR) resistance. A suitable host strain for DHFR selection can be CHO strain DX-B11, which is deficient in DHFR (Urlaub and Chasin, Proc. Natl. Acad. Sci. USA 77:4216, 1980). A plasmid expressing the DHFR cDNA can be introduced into strain DX-B 11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273:113, 1978; Kaufman, Meth. in Enzymology, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., Animal Cell Technology, 1997, pp.529–534) and the tripartite leader (TPL) and VA gene RNAs from Adenovirus 2 (Gingeras et al., J. Biol. Chem. 257:13475, 1982). The internal ribosome entry site (IRES) sequences of viral origin allows dicistronic mRNAs to be translated efficiently (Oh and Sarnow, Current Opinion in Genetics and Development 3:295, 1993; Ramesh et al., Nucleic Acids Research 24:2697, 1996). Expression of a heterologous cDNA as part of a dicistronic mRNA followed by the gene for a selectable marker (e.g. DHFR) has been shown to improve transfectability of the host and expression of the heterologous cDNA (Kaufman, Meth. in Enzymology, 1990). Exemplary expression vectors that employ dicistronic mRNAs are pTR-DC/GFP described by Mosser et al., Biotechniques 22:150, 1997, and p2A5I described by Morris et al., Animal Cell Technology, 1997, pp.529–534.

A useful high expression vector, pCAVNOT, has been described by Mosley et al., Cell 59:335, 1989. Other expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984, has been deposited as ATCC 39890. Additional useful mammalian expression vectors are known in the art.

Regarding signal peptides that may be employed in producing Tek polypeptides, the native Tek signal peptide may used or it may be replaced by a heterologous signal peptide or leader sequence, if desired. The choice of signal peptide or leader may depend on factors such as the type of host cells in which the recombinant Tek is to be produced. Examples of heterologous signal peptides that are functional in mammalian host cells include the signal sequence for interleukin-7 (IL-7) described in United States Patent 4,965,195, the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Using the techniques of recombinant DNA including mutagenesis and the polymerase chain reaction (PCR), the skilled artisan can produce DNA sequences that encode Tek polypeptides comprising various additions or substitutions of amino acid residues or sequences, or deletions of terminal or internal residues or sequences, including Tek fragments, variants, derivatives, and fusion polypeptides.

Transgenic animals, including mice, goats, sheep, and pigs, and transgenic plants, including tobacco, tomato, legumes, grasses, and grains, may also be used as bioreactors for the production of Tek polypeptides, including soluble Tek polypeptides. In the case of transgenic animals, it is particularly advantageous to construct a chimeric DNA including a Tek coding sequence operably linked to cis-acting regulatory sequences that promote expression of the soluble Tek in milk and/or other body fluids (see, e.g., U.S. Pat. No. 5,843,705; U.S. Pat. No. 5,880,327). In the case of transgenic plants it is particularly advantageous to produce Tek in a particular cell type, tissue, or organ (see, e.g., U.S. Pat. No. 5,639,947; U.S. Pat. No. 5,889,189).

The skilled artisan will recognize that the procedure for purifying expressed soluble Tek polypeptides will vary according to the host system employed, and whether or not the recombinant polypeptide is secreted. Soluble Tek polypeptides may be purified using methods known in the art, including one or more concentration, salting-out, ion exchange, hydrophobic interaction, affinity purification, HPLC, or size exclusion chromatography steps. Fusion polypeptides comprising Fc moieties (and multimers formed therefrom) offer the advantage of facile purification by affinity chromatography over Protein A or Protein G columns.

E. Tek Antibodies

One aspect of the present invention relates to the antigenic epitopes of the Tek extracellular domain. Such epitopes are useful for raising antibodies, and in particular the blocking monoclonal antibodies described in more detail below. Such epitopes or variants thereof can be produced using techniques well known in the art such as solid-phase synthesis, chemical or enzymatic cleavage of a polypeptide, or using recombinant DNA technology. As exemplified below, the Inventors have determined that the Tek extracellular domain comprises at least three epitopes, and that antibodies generated against a deleted form of the Tek extracellular domain can compete with Tek ligands for binding to Tek.

The claimed invention encompasses compositions and uses of antibodies that are immunoreactive with Tek polypeptides. Such antibodies "bind specifically" to Tek polypeptides, meaning that they bind via antigen-binding sites of the antibody as compared to non-specific binding interactions. The terms "antibody" and "antibodies" are used herein in their broadest sense, and include, without limitation, intact monoclonal and polyclonal antibodies as well as fragments such as Fv, Fab, and F(ab')2 fragments, single-chain antibodies such as scFv, and various chain combinations. The antibodies of the present invention are preferably humanized, and more preferably human. The antibodies may be prepared using a variety of well-known methods including, without limitation, immunization of animals having native or transgenic immune repertoires, phage display, hybridoma and recombinant cell culture, and transgenic plant and animal bioreactors.

Both polyclonal and monoclonal antibodies may be prepared by conventional techniques. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide, harvesting spleen cells from the immunized animal, fusing said spleen cells to a myeloma cell line, thereby generating hybridoma cells, and identifying a hybridoma cell line that produces a monoclonal antibody that binds the polypeptide. The monoclonal antibodies produced by hybridomas may be recovered by conventional techniques.

The monoclonal antibodies of the present invention include chimeric antibodies, e.g., "humanized" versions of antibodies originally produced in mice or other non-human species. A humanized antibody is an engineered antibody that typically comprises the variable region of a non-human (e.g., murine) antibody, or at least complementarity determining regions (CDRs) thereof, and the remaining immunoglobulin portions derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (TIPS 14:139, May, 1993). Such humanized antibodies may be prepared by known techniques and offer the advantage of reduced immunogenicity when the antibodies are administered to humans.

Procedures that have been developed for generating human antibodies in non-human animals may be employed in producing antibodies of the present invention. The antibodies may be partially human or preferably completely human. For example, transgenic mice into which genetic material encoding one or more human immunoglobulin chains has been introduced may be employed. Such mice may be genetically altered in a variety of ways. The genetic manipulation may result in human immunoglobulin polypeptide chains replacing endogenous immunoglobulin chains in at least some, and preferably virtually all, antibodies produced by the animal upon immunization.

Mice in which one or more endogenous immunoglobulin genes have been inactivated by various means have been prepared. Human immunoglobulin genes have been introduced into the mice to replace the inactivated mouse genes. Antibodies produced in the animals incorporate human immunoglobulin polypeptide chains encoded by the human genetic material introduced into the animal. Examples of techniques for the production and use of such transgenic animals to make antibodies (which are sometimes called "transgenic antibodies") are described in U.S. Pat. Nos. 5,814,318, 5,569,825, and 5,545,806, which are incorporated by reference herein.

F. Therapeutic Methods

The disclosed polypeptides, compositions, and methods are used to inhibit angiogenesis or other Tek-mediated responses in a mammal in need of such treatment. The term "Tek-mediated response" includes any cellular, physiological, or other biological response that is caused at least in part by the binding of a Tek ligand to Tek, or which may be inhibited or suppressed, in whole or in part, by blocking a Tek ligand from binding to Tek. The treatment is advantageously administered in order to prevent the onset or the recurrence of a disease or condition mediated by angiogenesis, or to treat a mammal that has a disease or condition mediated by angiogenesis. Diseases and conditions mediated by angiogenesis include but are not limited to ocular disorders, malignant and metastatic conditions, and inflammatory diseases.

Among the ocular disorders that can be treated according to the present invention are eye diseases characterized by ocular neovascularization including, but not limited to, diabetic retinopathy (a major complication of diabetes), retinopathy of prematurity (this devastating eye condition, that frequently leads to chronic vision problems and carries a high risk of blindness, is a severe complication during the care of premature infants), neovascular glaucoma, retinoblastoma, retrolental fibroplasia, rubeosis, uveitis, macular degeneration, and corneal graft neovascularization. Other eye inflammatory diseases, ocular tumors, and diseases associated with choroidal or iris neovascularization can also be treated according to the present invention.

The present invention can also be used to treat malignant and metastatic conditions such as solid tumors. Solid tumors include both primary and metastatic sarcomas and carcinomas.

The present invention can also be used to treat inflammatory diseases including, but not limited to, arthritis, rheumatism, and psoriasis.

Other diseases and conditions that can be treated according to the present invention include benign tumors and preneoplastic conditions, myocardial angiogenesis, hemophilic joints, scleroderma, vascular adhesions, atherosclerotic plaque neovascularization, telangiectasia, and wound granulation.

In addition to polypeptides comprising a fragment of Tek extracellular domain, soluble Tek multimers, and antibodies that bind to the Tek extracellular domain, other forms of Tek antagonists can also be administered to achieve a therapeutic effect. Examples of other forms of Tek antagonists include other antibodies such as antibodies against a Tek ligand, antisense nucleic acids, ribozymes, muteins, aptamers, and small molecules directed against Tek or against one or more of the Tek ligands.

The methods according to the present invention can be tested in in vivo animal models to confirm the desired prophylactic or therapeutic activity, as well as to determine the optimal therapeutic dosage, prior to administration to humans.

The amount of a particular Tek antagonist that will be effective in a particular method of treatment depends upon age, type and severity of the condition to be treated, body weight, desired duration of treatment, method of administration, and other parameters. Effective dosages are determined by a physician or other qualified medical professional. Typical effective dosages are about 0.01 mg/kg to about 100 mg/kg body weight. In some preferred embodiments the dosage is about 0.1–50 mg/kg; in some preferred embodiments the dosage is about 0.5–10 mg/kg. The dosage for local administration is typically lower than for systemic administration. In some embodiments a single administration is sufficient; in some embodiments the Tek antagonist is administered as multiple doses over one or more days.

The Tek antagonists are typically administered in the form of a pharmaceutical composition comprising one or more pharmacologically acceptable carriers. Pharmaceutically acceptable carriers include diluents, fillers, adjuvants, excipients, and vehicles which are pharmaceutically acceptable for the route of administration, and may be aqueous or oleaginous suspensions formulated using suitable dispersing, wetting, and suspending agents.

Pharmaceutically acceptable carriers are generally sterile and free of pyrogenic agents, and may include water, oils, solvents, salts, sugars and other carbohydrates, emulsifying agents, buffering agents, antimicrobial agents, and chelating agents. The particular pharmaceutically acceptable carrier and the ratio of active compound to carrier are determined by the solubility and chemical properties of the composition, the mode of administration, and standard pharmaceutical practice.

The Tek antagonists are administered to the patient in a manner appropriate to the indication. Thus, for example, a Tek antagonist, or a pharmaceutical composition thereof, may be administered by intravenous, transdermal, intradermal, intraperitoneal, intramuscular, intranasal, epidural, oral, topical, subcutaneous, intracavity, sustained release from implants, peristaltic routes, or by any other suitable technique. Parenteral administration is preferred.

In certain embodiments of the claimed invention, the treatment further comprises treating the mammal with one or more additional chemotherapeutic agents. The additional chemotherapeutic agent(s) may be administered prior to, concurrently with, or following the administration of the Tek antagonist. The use of more than one chemotherapeutic agent is particularly advantageous when the mammal that is being treated has a solid tumor. In some embodiments of the claimed invention, the treatment further comprises treating the mammal with radiation. Radiation, including brachytherapy and teletherapy, may be administered prior to, concurrently with, or following the administration of the second chemotherapeutic agent(s) and/or Tek antagonist.

When the mammal that is being treated has a solid tumor, the method preferably includes the administration of, in addition to a Tek antagonist, one or more chemotherapeutic agents selected from the group consisting of alkylating agents, antimetabolites, vinca alkaloids and other plant-derived chemotherapeutics, nitrosoureas, antitumor antibiotics, antitumor enzymes, topoisomerase inhibitors, platinum analogs, adrenocortical suppressants, hormones, hormone agonists and antagonists, antibodies, immunotherapeutics, blood cell factors, radiotherapeutics, and biological response modifiers.

In some preferred embodiments the method includes administration of, in addition to a Tek antagonist, one or more chemotherapeutic agents selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, and vinblastine, lymphokines and cytokines such as interleukins, interferons (including alpha, beta, or delta), and TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, and fluoxymesterone.

In some preferred embodiments the method includes administration of, in addition to a Tek antagonist, one or more chemotherapeutic agents, including various soluble forms thereof, selected from the group consisting of Flt3 ligand, CD40 ligand, interleukin-2, interleukin-12, 4-1BB ligand, anti-4-1BB antibodies, TNF antagonists and TNF receptor antagonists including TNFR/Fc, TWEAK antagonists and TWEAK-R antagonists including TWEAK-R/Fc, TRAIL, VEGF antagonists including anti-VEGF antibodies, VEGF receptor (including VEGF-R1 and VEGF-R2, also known as Flt1 and Flk1 or KDR) antagonists, and CD148 (also referred to as DEP-1, ECRTP, and PTPRJ, see Takahashi et al., J. Am. Soc. Nephrol. 10:2135–45, 1999) agonists.

In some preferred embodiments the Tek antagonists of the invention are used as a component of, or in combination with, "metronomic therapy," such as that described by Browder et al. and Klement et al. (Cancer Research 60:1878, 2000; J. Clin. Invest. 105(8):R15, 2000; see also Barinaga, Science 288:245, 2000).

The polypeptides, compositions, and methods of the present invention may be used as a first line treatment, for the treatment of residual disease following primary therapy, or as an adjunct to other therapies including chemotherapy, surgery, radiation, and other therapeutic methods known in the art.

EXAMPLES

The following examples are intended to illustrate particular embodiments and not to limit the scope of the invention.

Example 1

Recombinant Production of Soluble Tek/Fc Fusion Polypeptides

The molecular cloning of a cDNA encoding the human receptor tyrosine kinase (RTK) Tek (ork, Tie2) is described in U.S. Pat. No. 5,447,860. The Tek cDNA (deposited with the American Type Culture Collection under the terms of the Budapest Treaty on May 28, 1992, Accession No. ATCC 69003) encodes 1124 amino acids, including a signal peptide, an N-terminal extracellular domain, a transmembrane domain, and a C-terminal cytoplasmic domain. Based on sequence analysis, the signal peptide is predicted to encompass residues 1–18, the N-terminal extracellular domain is predicted to encompass residues 19–745, the transmembrane domain is predicted to encompass residues 746–772, and the C-terminal cytoplasmic domain is predicted to encompass residues 773–1124. The extracellular domain includes two immunoglobulin (Ig)-like loops, a region containing three EGF-like cysteine repeats (between residues 211–340), and a region containing three fibronectin type III (FNIII) motifs (between residues 440–733). Tek cDNA was used to construct recombinant expression vectors for the production of various Tek/Fc fusion polypeptides.

To construct a nucleic acid encoding the full length Tek extracellular domain fused to Fc, a nucleic acid encoding the N-terminal 745 amino acids from Tek, including the Tek leader (signal peptide) and extracellular domain, was fused to a nucleic acid encoding a 232 amino acid Fc portion from human IgG1. The amino acid sequence of the Tek/Fc fusion polypeptide encoded by this construct is shown as SEQ ID NO:1. In SEQ ID NO:1, residues 1–18 are the predicted signal peptide (predicted to be cleaved upon secretion from the cell; the actual cleavage site was identified by N-terminal sequence analysis, see below), residues 19–745 are the Tek extracellular domain, and residues 746–977 are the Fc portion. Upon insertion into a mammalian expression vector, and expression in and secretion from a mammalian host cell, this construct produced a polypeptide designated Tek745/Fc. Based on the predicted signal peptide cleavage site, the amino acid sequence of Tek745/Fc was predicted to be residues 19–977 of SEQ ID NO:1.

To construct a nucleic acid encoding a fragment of the Tek extracellular domain fused to Fc, a nucleic acid encoding the N-terminal 472 amino acids from Tek, including the Tek leader (signal peptide) and a deleted extracellular domain, was fused to a nucleic acid encoding a 232 amino acid Fc portion from human IgG1. The amino acid sequence of the Tek/Fc fusion polypeptide encoded by this construct is shown as SEQ ID NO:2. In SEQ ID NO:2, residues 1–18 are the predicted signal peptide (predicted to be cleaved upon secretion from the cell; the actual cleavage site was identified by N-terminal sequence analysis, see below), residues 19–472 are the fragment of the Tek extracellular domain, and residues 473–704 are the Fc portion. Upon insertion into a mammalian expression vector, and expression in and secretion from a mammalian host cell, this construct produced a polypeptide designated Tek472/Fc. Based on the predicted signal peptide cleavage site, the amino acid sequence of Tek472/Fc was predicted to be residues 19–704 of SEQ ID NO:2.

Nucleic acids encoding each of the Tek/Fc fusion polypeptides were inserted into mammalian expression vectors, and each vector was transfected into CHO cells. After amplification, stably transfected CHO cell lines were cultured under conditions promoting the expression and secretion of the recombinant fusion polypeptides and the Tek/Fc fusion polypeptides were recovered and isolated from the culture medium. N-terminal sequence analysis determined that the secreted polypeptide designated Tek745/Fc had an N-terminus corresponding to residue 23 (alanine) of SEQ ID NO:1. N-terminal sequence analysis determined that the secreted polypeptide designated Tek472/Fc had an N-terminus corresponding to residue 23 (alanine) of SEQ ID NO:2.

Anti-angiogenic activity of the Tek/Fc fusion polypeptides is demonstrated in the in vitro and in vivo systems described in Examples 2–6.

Example 2

Activity of Tek/Fc In a Wound Closure Assay

A planar endothelial cell migration (wound closure) assay was used to quantitate the inhibition of angiogenesis by Tek/Fc in vitro. In this assay, endothelial cell migration is measured as the rate of closure of a circular wound in a cultured cell monolayer. The rate of wound closure is linear, and is dynamically regulated by agents that stimulate and inhibit angiogenesis in vivo.

Primary human renal microvascular endothelial cells, HRMEC, were isolated, cultured, and used at the third passage after thawing, as described in Martin et al., In Vitro Cell Dev Biol 33:261, 1997. Replicate circular lesions, "wounds," (600–800 micron diameter) were generated in confluent HRMEC monolayers using a silicon-tipped drill press. At the time of wounding the medium (DMEM+1% BSA) was supplemented with 20 ng/ml PMA (phorbol-12-myristate-13-acetate), 10 μg/ml Tek472/Fc, or combinations of 20 ng/ml PMA and 0.001–10 μg/ml Tek472/Fc. The residual wound area was measured as a function of time (0–12 hours) using a microscope and image analysis software (Bioquant, Nashville, Tenn.). The relative migration rate was calculated for each agent and combination of agents by linear regression of residual wound area plotted over time. The results are shown in FIG. 1. Tek472/Fc inhibited PMA-induced endothelial migration in a dose responsive manner, reducing the rate of migration to unstimulated levels at 10 μg/ml.

Example 3

Activity of Tek/Fc In a Corneal Pocket Assay

A mouse corneal pocket assay was used to quantitate the inhibition of angiogenesis by Tek/Fc in vivo. In this assay, agents to be tested for angiogenic or anti-angiogenic activity are immobilized in a slow release form in a hydron pellet, which is implanted into micropockets created in the corneal epithelium of anesthetized mice. Vascularization is measured as the appearance, density, and extent of vessel ingrowth from the vascularized corneal limbus into the normally avascular cornea.

Figure 2:
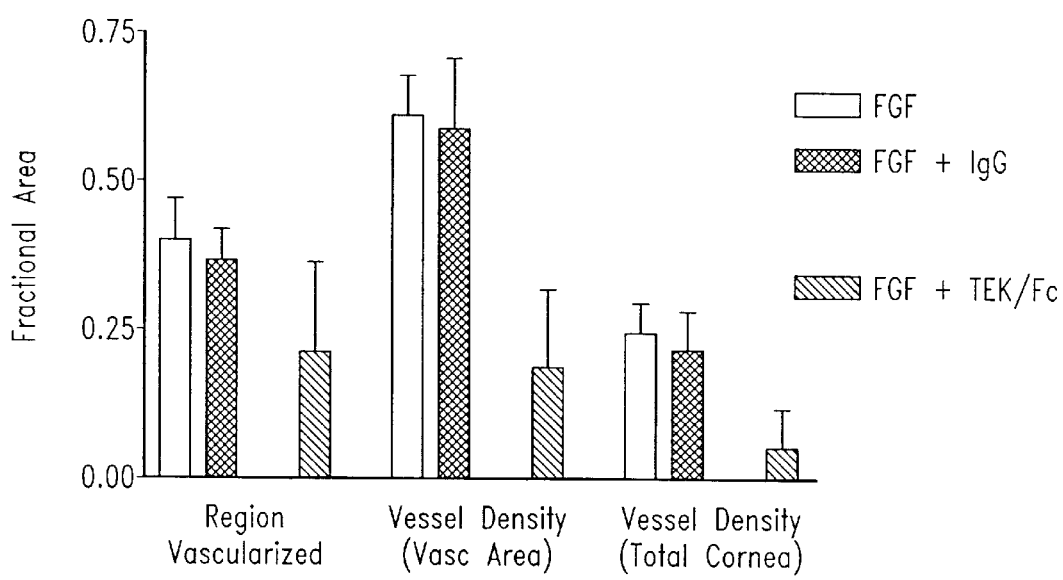
FIG. 2 shows inhibition by Tek472/Fc of angiogenesis in a corneal pocket assay.

Hydron pellets, as described in Kenyon et al., Invest Opthamol. & Visual Science 37:1625, 1996, incorporated sucralfate with bFGF (90 ng/pellet), bFGF and IgG (11 μg/pellet, control), or bFGF and Tek472/Fc (12.8 μg). The pellets were surgically implanted into corneal stromal micropockets created by micro-dissection 1 mm medial to the lateral corneal limbus of 6–8 week old male C57BL mice. After five days, at the peak of neovascular response to bFGF, the corneas were photographed, using a Zeiss slit lamp, at an incipient angle of 35–50° from the polar axis in the meridian containing the pellet. Images were digitized and processed by subtractive color filters (Adobe Photoshop 4.0) to delineate established microvessels by hemoglobin content. Image analysis software (Bioquant, Nashville, Tenn.) was used to calculate the fraction of the corneal image that was vascularized, the vessel density within the vascularized area, and the vessel density within the total cornea. The results are shown in FIG. 2. Tek472/Fc (50 pmol) inhibited bFGF (3 pmol)-induced corneal angiogenesis, reducing the vascular density to 30% of that induced by FGF alone.

Example 4

Inhibition of Neovascularization by Tek/Fc in a Murine Transplant Model Survival of heterotopically transplanted cardiac tissue from one mouse donor to the ear skin of another genetically similar mouse requires adequate neovascularization by the transplanted heart and the surrounding tissue, to promote survival and energy for cardiac muscle function. Inadequate vasculature at the site of transplant causes excessive ischemia to the heart, tissue damage, and failure of the tissue to engraft. Agents that antagonize the angiopoietins and endothelial specific factors involved in endothelial cell migration and vessel formation can decrease angiogenesis at the site of transplant, thereby limiting graft tissue function and ultimately engraftment itself.

The following studies were carried out, utilizing a murine heterotopic cardiac isograft model, in order to demonstrate the antagonistic effects of Tek/Fc on neovascularization. In all experiments, female BALB/c (≈12 weeks of age) recipients received neonatal heart grafts from donor mice of the same strain.

A. Tek/Fc at 500 μg/Dav Dose

In each of three experiments, the donor heart tissue was engrafted into the left ear pinnae of the recipient on day 0 and the mice were divided into two groups. The control group received human IgG (Hu IgG) while the other group received human Tek472/Fc, both intraperitoneally at 500 μg per day. All treatments began on day 0 and continued for five consecutive days. The functionality of the grafts was determined by monitoring visible pulsatile activity on days 7 and 14 post-engraftment.

Table 1 shows the cumulative results from the three experiments. All 8 mice receiving Hu IgG had functioning grafts on days 7 and 14, indicating 100% engraftment. The Tek472/Fc treated mice initially demonstrated no functional activity, indicative of diminished engraftment, with only 36% having functioning grafts at day 7. By day 14, ten days after cessation of Tek472/Fc treatment, 82% of the mice had functioning grafts.

TABLE 1

| Functional Engraftment at Days 7 and 14 | | | |
|---|---|---|---|
| Total | Treatment | Day 7 | Day 14 |
| N = 8 | Hu IgG | 8/8 (100%) | 8/8 (100%) |
| N = 11 | Tek472/Fc | 4/11 (36%) | 9/11 (82%) |

Histological studies on the transplanted hearts of mice receiving the Tek/Fc showed increased edema at the site of transplant, indicative of vascular leakage, and decreased host and donor tissue vasculature staining (Factor VIII) as compared to that observed in transplanted hearts from mice receiving the control protein IgG.

This experiment showed that treatment with Tek472/Fc severely compromised cardiac isograft function and prevented engraftment of tissue in 64% of mice at day 7 after a 5 day course of therapy.

B. Tek/Fc Dose Titration

Three different doses of Tek/Fc were tested in the cardiac isograft model described above. Each test group contained four female BALB/c mice. The control group received human IgG (Hu IgG), intraperitoneally, at 500 μg per day for five consecutive days. The Tek/Fc groups received human Tek472/Fc, intraperitoneally, at 90, 250, or 500 μg per day for five consecutive days. The functionality of the grafts was determined by monitoring visible pulsatile activity on post-engraftment days 7, 11, 14, 17, and 21. The results are shown in Table 2.

TABLE 2

| Functional Engraftment Following Dose Titration with Tek | | | | | |
|---|---|---|---|---|---|
| Treatment | Day 7 | Day 11 | Day 14 | Day 17 | Day 21 |
| Hu IgG 500 μg | 100* | 100 | 100 | 100 | 100 |
| Tek472/Fc 90 μg | 75 | 00 | 100 | 100 | 100 |
| Tek472/Fc 250 μg | 25 | 75 | 75 | 100 | 100 |
| Tek472/Fc 500 μg | 25 | 75 | 75 | 75 | 75 |

*all results are reported as percent of mice with pulsatile heart grafts

A similar magnitude of cardiac isograft engraftment disruption was observed at both the 250 μg and 500 μg doses of Tek/Fc, as compared to Hu IgG control where no effect on engraftment was observed. A small, albeit significantly insignificant, reduction in engraftment was observed at the 90 µg dose.

C. Tek/Fc In Combination With a VEGF Antagonist

The anti-angiogenic activity of Tek/Fc in combination with an anti-murine VEGF monoclonal antibody was tested in the cardiac isograft model. The antibody, JH121 (Lab Vision Corporation, Fremont, Calif.), is an $IgG_1$ that recognizes various isoforms of VEGF and neutralizes the bioactivity of VEGF. Each treatment group contained five mice. The mice were administered control protein (Hu IgG, 250 micrograms per day), anti-murine VEGF antibody (100 micrograms per day), Tek472/Fc (250 micrograms per day), or the combination of anti-murine VEGF antibody (100 micrograms per day) and Tek472/Fc (250 micrograms per day) intraperitoneally for five consecutive days starting at day 0, the day of the cardiac transplant. The effect of each treatment on cardiac isoengraftment/neovascularization was compared by determining functional engraftment on day 7 post transplant. The results are shown in Table 3.

TABLE 3

Functional Engraftment Following Treatment With Tek/Fc and Anti-VEGF Antibody

| Treatment | Engraftment at Day 7 |
|---|---|
| Hu IgG 250 µg | 5/5 (100%) |
| Anti-VEGF 100 µg | 2/5 (40%) |
| Tek472/Fc 250 µg | 2/5 (40%) |
| Anti-VEGF and Tek472/Fc | 0/5 (0%) |

Both anti-VEGF and Tek/Fc were effective antiangiogenic agents, and treatment with the two agents in combination had a more pronounced biological effect than either agent administered alone. These results indicate that in combination lower doses of Tek antagonists and/or VEGF antagonists may be used to achieve significant biological antiangiogenic responses in vivo.

Example 5

Treatment of Tumors With Tek472/Fc

A. Tek/Fc Alone and In Combination With a Second Chemotherapeutic Agent

Tek472/Fc was administered alone, and in combination with Flt3L, to treat mice bearing 87 fibrosarcoma or B10.2 fibrosarcoma tumors. The B10.2 and 87 tumors are of the progressor phenotype, i.e. they grow progressively in normal mice. The B10.2 fibrosarcoma was induced by subcutaneous implantation of a paraffin pellet containing 5 mg of methylcholanthrene in C57BL mice (Lynch and Miller, Eur. J. Immunol., 21:1403, 1991). The 87 fibrosarcoma is a progressor variant of a tumor induced by chronic exposure of C3H/HeN mice to UVB irradiation. To innoculate tumors in mice for these experiments, $5 \times 10^5$ cells were injected (day 0) intradermally in the abdomen (see, also, Borges et al., J. Immunol. 163:1289, 1999, which is incorporated herein by reference).

Figure 3:
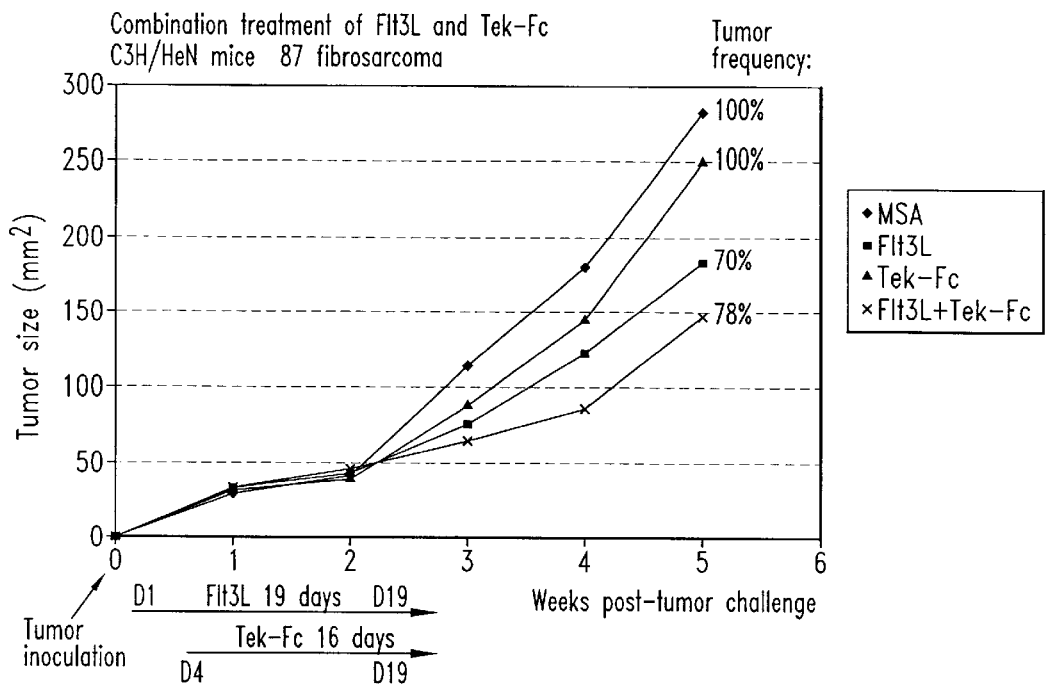
FIG. 3 shows tumor growth after treatment with Tek472/Fc, Flt3L, and combinations of Tek472/Fc and Flt3L, in mice with 87 fibrosarcoma tumors.

The 87 fibrosarcoma tumors in C3H/HeN mice were treated with MSA (murine serum albumin, control), Tek/Fc (312 µ/day, days 4–19 after tumor cell injection), Flt3L (10 µg/day, days 1–19 after tumor cell injection), or a combination of Tek/Fc and Flt3L (Tek/Fc at 312 µg/day, days 4–19; Flt3L at 10 µg/day, days 1–19 after tumor cell injection). Each treatment group consisted of ten mice. Tumor frequency and tumor size were measured weekly for five weeks. The results are shown in FIG. 3. Mice treated with the combination of Tek/Fc and Flt3L showed the slowest tumor growth rates. In week 6 an additional animal in the Tek/Fc plus Flt3L group rejected the tumor, decreasing the tumor frequency to 68%. Based upon the results of this experiment, the combination of Tek/Fc and Flt3L was used to treat pre-existing B 10.2 fibrosarcoma tumors.

Figure 4:
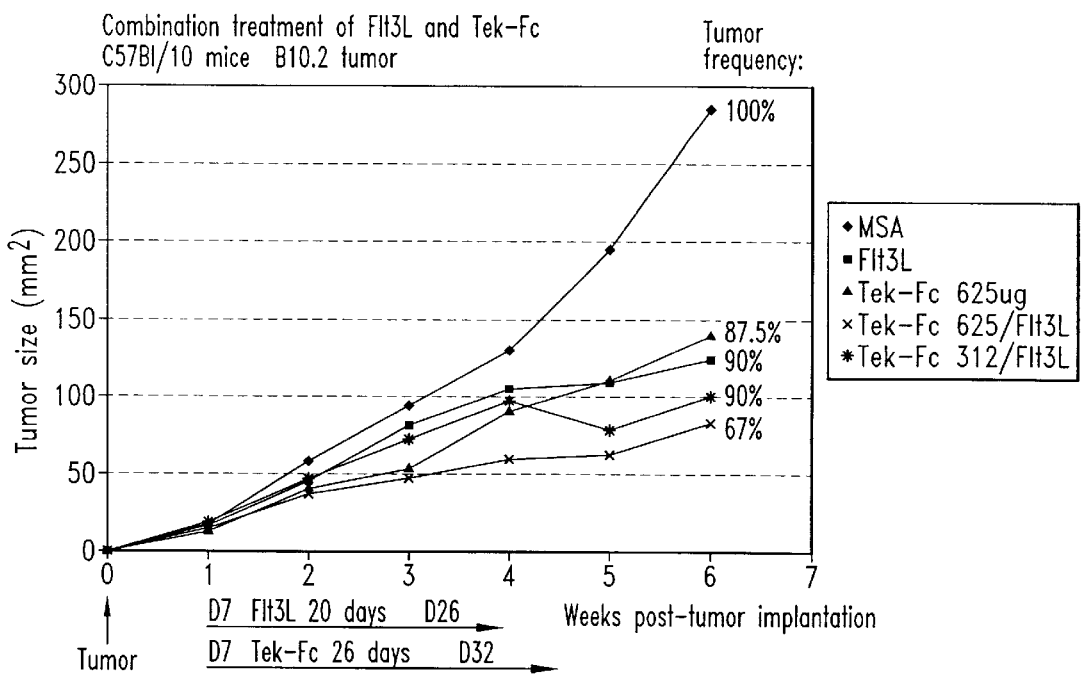
FIG. 4 shows tumor growth after treatment with Tek472/Fc, Flt3L, and combinations of Tek472/Fc and Flt3L in mice with B 10.2 fibrosarcoma tumors.

The B10.2 fibrosarcoma tumors in C57BL/10 mice were treated with MSA (control), Tek/Fc (625 µg/day, days 7–32 after tumor cell injection), Flt3L (10 µg/day, days 7–26 after tumor cell injection), or a combination of Tek/Fc and Flt3L (Tek/Fc at 312.5 or 625 µg/day, days 7–32; Flt3L at 10 µg/day, days 7–26 after tumor cell injection). Each treatment group consisted of ten mice. Tumor frequency and tumor size were measured weekly for six weeks. The results are shown in FIG. 4. Mice treated with both combinations of Tek/Fc and Flt3L showed reduced tumor growth rates; mice treated with 625 µg/day Tek/Fc in combination with Flt3L showed the slowest tumor growth rate.

B. Tek/Fc Alone and In Combination With Ionizing Radiation

3LL Lewis lung adenocarcinoma ($1 \times 10^5$ cells) were innoculated in the foot pad of C57B1/6 mice. Mice with palpable tumors (2–3 weeks after innoculation, <5 mm diameter) were treated with either Hu IgG or Tek472/Fc (500 µg, intraperitoneally, per day) for 21 days. Initial tumor volume (Vo) was established for each mouse prior to the initiation of therapy. Radiation therapy (RT) was started on day 8 of Tek472/Fc and/or IgG treatment. The RT regimen comprised 6 Gy/day for 4 days/week to a total of 48 Gy. Tumor size was determined biweekly. Animals were sacrificed one week after the completion of Tek472/Fc treatment (day 28), and the mean relative or fractional tumor volume (Vf/Vo) was determined. Vf/Vo is equal to the final tumor volume of the primary footpad tumor in each mouse on day 28 divided by the initial tumor volume determined on the day of therapy initiation.

The results are shown in Tables 4 and 5. Administration of Tek/Fc, as a single agent, to mice bearing established 3LL tumors decreased tumor growth by almost 50% compared to Hu IgG treatment alone (p=0.035). Radiation therapy was also effective at slowing tumor growth in this 3LL model. When Tek/Fc treatment was combined with radiation therapy, tumor growth was inhibited significantly more than was the tumor growth after Tek/Fc treatment alone or radiation+IgG treatment (p<0.001).

TABLE 4

Summary of Fractional Tumor Volume ($V_f/V_0$) as a Function of Treatment

| Treatment Group | Number (n) | Mean $V_f/V_0$ | S.D. | SEM |
|---|---|---|---|---|
| Control | 5 | 62.51 | 34.88 | 15.59 |
| IgG | 4 | 42.19 | 11.92 | 5.33 |
| RT | 5 | 20.93 | 9.5 | 4.25 |
| IgG + RT | 15 | 14.98 | 5.77 | 1.49 |
| Tek472/Fc | 10 | 24.85 | 12.43 | 3.93 |
| Tek472/Fc + RT* | 14 | 6.76 | 3.29 | 0.88 |

*One way analysis of variance, p < 0.001

TABLE 5

Comparison Between Groups*

| Treatment Group | p Value |
| --- | --- |
| Tek/Fc vs. Control (no treatment) | 0.008 |
| Tek/Fc vs. IgG | 0.035 |
| Tek/Fc vs. RT | 0.548 |
| Tek/Fc + RT vs. Tek/Fc | <0.001 |
| Tek/Fc + RT vs. RT | <0.001 |
| Tek/Fc + RT vs. IgG + RT | <0.001 |

*p values after t-test

Example 6

Binding of Tek/Fc Fusion Polypeptides to Angiopoietin

Both Tek745/Fc and Tek472/Fc were examined for the ability to bind the human Tek ligand angiopoietin 2 (Ang2), using a solid-phase plate binding assay based on time-resolved fluorescence. Comparison of binding to human Ang2 with the two different forms of soluble Tek/Fc revealed that Tek472/Fc bound significantly better (21-fold better) to Ang2 than did Tek745/Fc.

Figure 5:
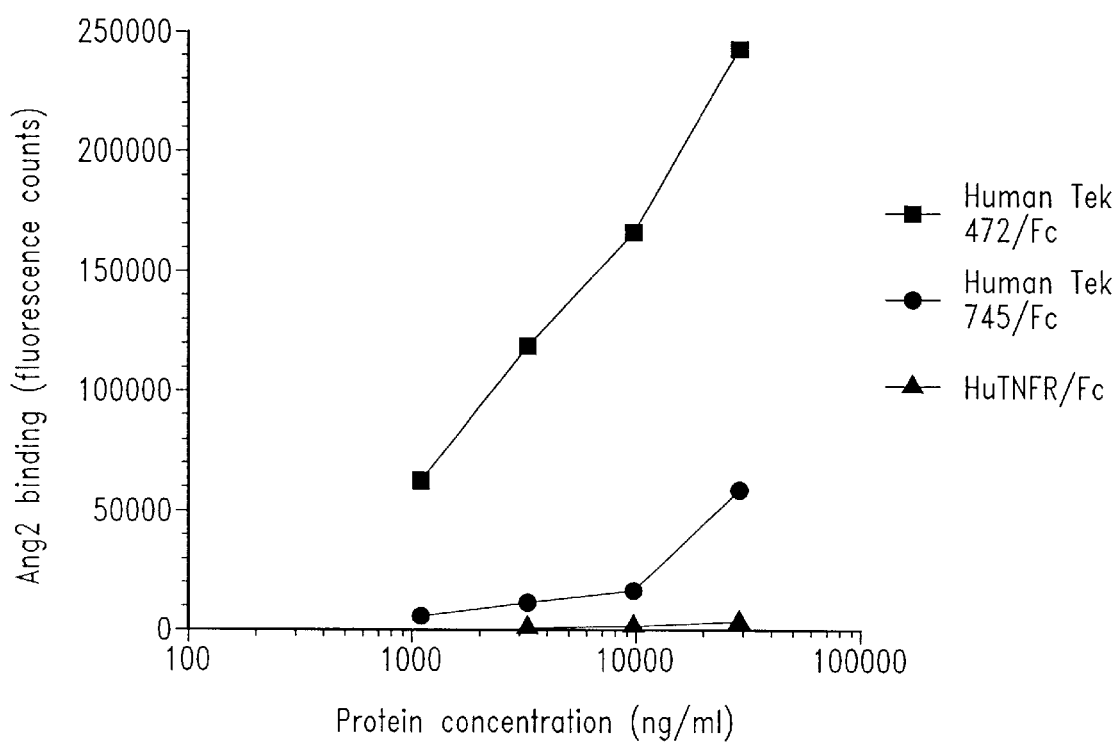
FIG. 5 shows the binding of Tek472/Fc and Tek745/Fc to human angiopoietin-2.

Low fluorescence 8×12 strip microtiter plate wells (Perkin-Wallac, Ackron, Ohio) were incubated with human Ang2 (R&D systems) at 500 ng/ml (100 µl) overnight at 2–8° C. The wells were then blocked by the addition of 100 µl of 1% BSA/PBS solution for 1 hour at room temperature. Following a 4×PBS-T (PBS-Tween 20 0.05%) wash, samples containing Tek745/Fc, Tek472/Fc, or TNFR/Fc (control/Fc) were titrated in diluent (1% BSA/PBS), in duplicate, beginning at 30 µg/ml in 3-fold dilutions. The samples were allowed to bind for 1 hour at room temperature with gentle agitation and then the unbound material was washed away 4× with PBS-T. Bound Tek/Fc was detected by adding goat anti human IgG-Europium conjugate (Perkin-Wallac), diluted to 100 ng/ml in assay buffer, to the wells and incubating for 30 minutes at room temperature. Unbound goat anti-human IgG-Europium was removed by a 4×PBS-T wash. Following the wash 150 µl of Enhancement solution (Perkin Wallac) was added to each well and the plate allowed to incubate at room temperature for a minimum of 5 minutes. Binding was determined by reading the fluorescence emitted from each well on a Victor II Multilabel counter equipped with software and light excitation/emission devices to measure Europium-derived fluorescence. The results, expressed as fluorescence counts, are shown in FIG. 5.

The TNFR/Fc control did not exhibit detectable binding (over that observed for background) to human Ang2. Both Tek472/Fc and Tek745/Fc bound to human Ang2 in a concentration dependent manner, but Tek472/Fc had a higher binding affinity. Tek472/Fc bound greater than 20-fold better than Tek745/Fc, based on mass concentration. Much higher concentrations of Tek745/Fc were required to achieve the same level of binding observed at lower concentrations of Tek472/Fc. The BC40K (the concentration of Tek/Fc required to achieve 40,000 fluorescence counts of huANG-2 binding) for Tek745/Fc was 20,596 ng/ml, compared to the BC40K for Tek472/Fc which was 994 ng/ml.

Example 7

Tek-Specific Blocking Monoclonal Antibodies

A. Antibodies to Tek472/Fc

Antibodies against "recombinant Tie2 extracellular domain-Fc fusion" have been described by Holmes et al., WO 00/18437. The present Inventors, in contrast, made antibodies against the deleted Tek extracellular domain fusion polypeptide Tek472/Fc. As shown in example 6, Tek472/Fc binds Tek ligand with higher affinity than does Tek745/Fc.

BALB/c mice were immunized with the Tek/Fc fusion polypeptide Tek472/Fc described in Example 1. Spleen cells were collected and used to prepare hybridomas using standard procedures. Hybridoma supernatants were screened, using ELISA, for the ability to bind (a) Tek472/Fc and (b) CV1 cells expressing human Tek. Positives were cloned two times, to insure monoclonality, then isotyped and reassayed for reactivity to Tek.

Three antibodies were chosen for further experiments: M530 (IgG2b isotype), M531 (IgG2b isotype), and M532 (IgG1 isotype). M530 and M531 appear to recognize the same epitope and M532 recognizes a second (different) epitope. M530 and M532 were therefore used as an antibody pair (e.g., for capture and detection) in various immunoassays. M530 was shown (by immunoprecipitation and by solid phase plate binding assays) to bind Tek745/Fc, Tek472/Fc, and to bind to naturally occurring Tek as expressed on the surface of human endothelial cells. The M530 antibody was further characterized in the binding and epitope mapping studies described in Example 8, below.

B. Additional Tek Antibodies

A workshop panel of putative endothelial cell-specific antibodies, which were not yet clustered, was obtained from the Human Leukocyte Differentiation Antigens (HLDA) Workshop. Some of the antibodies were generated by immunizing mice with human endothelial cells. One antibody in the panel was known to react with human Tek. These antibodies were further characterized in the binding and epitope mapping studies described in Example 8, below.

Example 8

Tek Antibody Binding to Tek and to Human Microvascular Endothelial Cells

A. Antibody Binding to Full Length Tek Extracellular Domain and to Endothelial Cells Using a solid phase binding assay (time resolved fluorescence, as described in Example 6), the huTek monoclonal antibody M530 described in Example 7A and eight monoclonal antibodies described in Example 7B (endothelial cell-specific antibodies numbered WS#70098, #70099, #70100, #70101, #70104, #70108, #70112, and putative Tek-specific antibody #70637) bound specifically to the full length Tek extracellular fusion polypeptide Tek745/Fc. An IgG1 negative control mAb (MOPC21) did not bind to Tek745/Fc over background. Two other endothelial cell-specific workshop antibodies (WS#70110 and #70115 did not detectably bind to Tek745/Fc.

Using flow cytometry, the human Tek monoclonal antibodies M530, M531, and M532 described in Example 7A and eight monoclonal antibodies described in Example 7B (endothelial cell-specific antibodies numbered #70098, #70099, #70100, #70101, #70104, #70108, #70112, and Tek-specific antibody #70637) were shown to bind to naturally occurring Tek as expressed on human endothelial cells (both human microvascular endothelial cells from adult skin and HUVEC).

B. Antibody Binding to a Tek Extracellular Domain Lacking FN3 Motifs The monoclonal antibody M530 described in Example 7A and seven monoclonal antibodies described in Example 7B (endothelial cell-specific antibodies numbered #70098, #70099, #70100, #70101. #70104, #70108, and #70112) bound specifically to the deleted Tek extracellular fusion polypeptide Tek472/Fc. Workshop antibodies #70637 (which bound to Tek745/Fc), #70110, and #70115 did not bind to Tek472/Fc.

C. Competitive Inhibition of Antibody Binding by Tek Ligands

Angiopoietin-1 (Ang1, Davis et al., Cell 87:1161, 1996) and Angiopoietin-2 (Ang2, Maisonpierre et al., Science 277:55, 1997) are two closely related Tek ligands. Both Ang1 and Ang2 bind with similar affinity to human Tek. The addition of a molar excess of Ang2 to EC cultures in the presence of Ang1 has been shown to inhibit Ang1 induced activation of Tek on endothelial cells via competition of Ang1 binding to endothelial cells (Maisonpierre et al., Science 277:55, 1997). A recombinant human angiopoietin-2 preparation was obtained from R&D Systems, Inc. (Minneapolis, Minn.). According to the manufacturer, the angiopoietin-2 preparation migrates as a 66 kDa protein in SDS-PAGE under both reducing and non-reducing conditions. Based on N-terminal amino acid sequencing, the preparation contains two peptides: a major polypeptide (75% of the total) having Asp68 as its N-terminus and a minor polypeptide (25% of the total) having Tyr19 as its N-terminus.

The ability of this Ang2 preparation to competitively inhibit the binding of Tek antibodies to Tek expressed on skin human microvascular endothelial cells was tested using flow cytometry.

Each mAb was added to 500,000 HMVEC-d at 5 µg/ml in 12×75 mm falcon tubes in duplicate and allowed to incubate for 15 minutes at 4° C. in binding medium. To one set of the duplicates, human Ang2 was added at 10 µg/ml (a five-fold molar excess) for an additional 30 minutes. The cells with the bound Tek mAb were then washed in 20 volumes of PBS-containing wash buffer. After the wash step, bound mouse mAb was detected by the addition of F(ab'2) sheep anti mouse IgG-PE fluorescent conjugate to the cells, followed by a 30 minute incubation at 4° C. and an additional 20 volume wash. Binding of the Tek mAb was measured by flow cytometric analysis on a single-laser FACSCAN (Becton Dickinson, Sunnyvale Calif.). The percent inhibition of antibody binding was calculated using the formula:

MFI (no Ang2)–MFI (+Ang2)/MFI (noAng2)×100.

The results are shown in Table 6.

TABLE 6

Inhibition of Tek Antibody Binding by Ang2

| Monoclonal Antibody 5 µg/ml | Percent Inhibition of Antibody Binding by Ang2 |
|---|---|
| negative control (MOPC-21) | 0 |
| binding control ($\alpha v \beta 3$) | 6.4 |
| M530 | 41.6 |
| #70098 | 45.9 |
| #70099 | 44.4 |
| #70100 | 0 |
| #70101 | 38.7 |
| #70104 | 6.3 |
| #70108 | 50.8 |
| #70112 | 47.6 |
| #70637 | 0 |

These results, inhibition of Tek antibody binding by Ang2, suggest that the M530, #70098, #70099, #70101, #70108, and #70112 antibodies bind at or near the Tek ligand binding site. The mAbs M530, WS#70099 and #70112 were also able to inhibit Ang2 binding (100 ng/ml) to recombinant human Tek472/Fc, by greater than 50% for mAb M530 and #70112 at concentrations of 10 µg/ml or greater and for mAb 70099 at concentrations of 3 µg/ml or greater.

In combination the binding results described in this example define at least three antibody epitopes in the human Tek extracellular domain, and exemplify the utility of preparing antibodies using a fragment of the Tek extracellular domain that lacks all or part of the region containing fibronectin type III (FNIII) motifs as an immunogen/target.

The relevant disclosures of publications cited herein are specifically incorporated by reference. The examples presented above are not intended to be exhaustive or to limit the scope of the invention. The skilled artisan will understand that variations and modifications and variations are possible in light of the above teachings, and such modifications and variations are intended to be within the scope of the invention.

We claim:

1. A nucleic acid encoding a polypeptide, wherein the polypeptide comprises a fragment of the Tek extracellular domain shown as residues 19–745 of SEQ ID NO: 1, wherein the fragment lacks at least the residues corresponding to residues 473–745 of SEQ ID NO:1, and wherein the fragment retains the ability to bind at least one Tek ligand.

2. The nucleic acid of claim 1, wherein the polypeptide has a higher binding affinity for a Tek ligand than does a polypeptide comprising full length Tek extracellular domain.

3. The nucleic acid of claim 2, wherein the polypeptide has at least a five-fold higher binding affinity for angiopoietin-2.

4. The nucleic acid of claim 2, wherein the polypeptide has at least a 21-fold higher binding affinity for angiopoietin-2.

5. The nucleic acid of claim 1, wherein the nucleic acid further comprises a sequence that encodes a signal peptide.

6. The nucleic acid of claim 1, wherein the nucleic acid further comprises a sequence that encodes a Fc polypeptide, a leucine zipper, or a peptide linker.

7. An expression vector comprising the nucleic acid of claim 1.

8. A host cell comprising the nucleic acid of claim 1.

9. A method of making a polypeptide comprising expressing a nucleic acid according to claim 1 in a recombinant host cell under conditions that permit expression of the polypeptide.

10. A nucleic acid encoding a polypeptide, wherein the polypeptide comprises a fragment of Tek extracellular domain that lacks all or part of the region containing fibronectin type III (FNIII) motifs and retains the ability to bind at least one Tek ligand, and wherein the fragment of Tek extracellular domain consists essentially of a sequence selected from the group consisting of:

(a) residues 1–472 of SEQ ID NO:2 and fragments thereof that bind a Tek ligand; and (b) sequences that are at least 90% identical to (a).

11. The nucleic acid of claim 10 wherein the fragment of Tek extracellular domain consists essentially of a sequence that is at least 95% identical to residues 23–472 of SEQ ID NO:2, or to a fragment thereof that binds a Tek ligand.

12. The nucleic acid of claim 11 wherein the fragment of Tek extracellular domain consists essentially of a sequence that is at least 98% identical to residues 23–472 of SEQ ID NO:2, or to a fragment thereof that binds a Tek ligand.

13. The nucleic acid of claim 12 wherein the fragment of Tek extracellular domain consists essentially of a sequence that is at least 99% identical to residues 23–472 of SEQ ID NO:2, or to a fragment thereof that binds a Tek ligand.

14. The nucleic acid of claim 12, wherein the nucleic acid further comprises a sequence that encodes a signal peptide.

15. The nucleic acid of claim 12, wherein the nucleic acid further comprises a sequence that encodes a Fc polypeptide, a leucine zipper, or a peptide linker.

16. An expression vector comprising the nucleic acid of claim 12.

17. A host cell comprising the nucleic acid of claim 12.

18. A method of making a polypeptide comprising expressing a nucleic acid according to claim 12 in a recombinant host cell under conditions that permit expression of the polypeptide.

19. The nucleic acid of claim 10 wherein the fragment of Tek exctracellular domain consists of residues 23–472 of SEQ ID NO:2.

20. The nucleic acid of claim 10 wherein the nucleic acid encodes residues 23–704 of SEQ ID NO:2.

21. The nucleic acid of claim 10, wherein the nucleic acid further comprises a sequence that encodes a signal peptide.

22. The nucleic acid of claim 10, wherein the nucleic acid further comprises a sequence that encodes a Fc polypeptide, a leucine zipper, or a peptide linker.

23. An expression vector comprising the nucleic acid of claim 10.

24. A host cell comprising the nucleic acid of claim 10.

25. A method of making a polypeptide comprising expressing a nucleic acid according to claim 10 in a recombinant host cell under conditions that permit expression of the polypeptide.

26. A nucleic acid that encodes a polypeptide having the sequence SEQ ID NO:2.

27. An expression vector comprising the nucleic acid of claim 26.

28. A host cell comprising the nucleic acid of claim 26.

29. A method of making a polypeptide comprising expressing a nucleic acid according to claim 26 in a recombinant host cell under conditions that permit expression of the polypeptide.

30. A nucleic acid comprising a region that encodes a polypeptide, wherein the region consists essentially of a sequence that is at least 90% identical to a sequence that encodes residues 1–472 of SEQ ID NO:2 or a fragment thereof and wherein the polypeptide binds a Tek ligand.

31. The nucleic acid of claim 30 wherein the sequence is at least 95% identical to a sequence that encodes residues 1–472 of SEQ ID NO:2 or a fragment thereof.

32. The nucleic acid of claim 31 wherein the sequence is at least 98% identical to a sequence that encodes residues 1–472 of SEQ ID NO:2 or a fragment thereof.

33. The nucleic acid of claim 32 wherein the sequence is at least 99% identical to a sequence that encodes residues 1–472 of SEQ ID NO:2 or a fragment thereof.

34. The nucleic acid of claim 32, wherein the nucleic acid further comprises a sequence that encodes a signal peptide.

35. The nucleic acid of claim 32, wherein the nucleic acid further comprises a sequence that encodes a Fc polypeptide, a leucine zipper, or a peptide linker.

36. An expression vector comprising the nucleic acid of claim 32.

37. A host cell comprising the nucleic acid of claim 32.

38. A method of making a polypeptide comprising expressing a nucleic acid according to claim 32 in a recombinant host cell under conditions that permit expression of the polypeptide.

39. The nucleic acid of claim 30, wherein the nucleic acid further comprises a sequence that encodes a signal peptide.

40. The nucleic acid of claim 30, wherein the nucleic acid further comprises a sequence that encodes a Fc polypeptide, a leucine zipper, or a peptide linker.

41. An expression vector comprising the nucleic acid of claim 30.

42. A host cell comprising the nucleic acid of claim 30.

43. A method of making a polypeptide comprising expressing a nucleic acid according to claim 30 in a recombinant host cell under conditions that permit expression of the polypeptide.

* * * * *

UNITED STATES PATENT AND TRADEMARK OFFICE
CERTIFICATE OF CORRECTION

PATENT NO. : 6,521,424 B2
APPLICATION NO. : 09/733764
DATED : February 18, 2003
INVENTOR(S) : Cerretti et al.

It is certified that error appears in the above-identified patent and that said Letters Patent is hereby corrected as shown below:

Column 4, Line 12, replace "B 10.2" with --B10.2--.

Column 20, Line 4, replace "500 ug/Dav Dose" with --500 ug/Day Dose--.

Column 22, Line 11, replace "B 10.2" with --B10.2--.

Column 24, Line 57, replace "(WS#70110 and #70115" with --(WS#70110 and #70115)--.

Column 25, Line 2, insert a new paragraph before the words, "The monoclonal antibody M530 described in...."

Column 25, Line 36, replace "4°C." with --4°C--.

Column 25, Line 43 replace "4°C." with --4°C--.

Signed and Sealed this

Twenty-second Day of August, 2006

JON W. DUDAS
*Director of the United States Patent and Trademark Office*